United States Patent
Conroy, Jr.

(10) Patent No.: US 7,246,620 B2
(45) Date of Patent: Jul. 24, 2007

(54) SYSTEM FOR MONITORING PILOT AND/OR PASSENGER OXYGEN SATURATION LEVELS AND ESTIMATING OXYGEN USAGE REQUIREMENTS

(76) Inventor: John D. Conroy, Jr., 3120 Fishing Creek Valley Rd., Harrisburg, PA (US) 17112

( * ) Notice: Subject to any disclaimer, the term of this patent is extended or adjusted under 35 U.S.C. 154(b) by 488 days.

(21) Appl. No.: 10/697,785

(22) Filed: Oct. 30, 2003

(65) Prior Publication Data

US 2004/0206353 A1    Oct. 21, 2004

Related U.S. Application Data

(63) Continuation-in-part of application No. 10/419,672, filed on Apr. 21, 2003.

(51) Int. Cl.
| | |
|---|---|
| A62B 7/00 | (2006.01) |
| A61M 16/00 | (2006.01) |
| A61B 5/00 | (2006.01) |
| B64D 11/00 | (2006.01) |

(52) U.S. Cl. ............................. 128/205.11; 128/204.29; 244/118.5; 600/323

(58) Field of Classification Search ........... 128/202.12, 128/202.22, 204.21, 204.22, 204.23, 205.23, 128/204.29, 205.11; 244/118.5; 600/323, 600/310, 532
See application file for complete search history.

(56) References Cited

U.S. PATENT DOCUMENTS

| | | | |
|---|---|---|---|
| 3,734,091 A | 5/1973 | Taplin | |
| 4,584,996 A | 4/1986 | Blum | |
| H001039 H * | 4/1992 | Tripp et al. ............ | 128/206.28 |
| H1039 H | 4/1992 | Tripp, Jr. et al. | |
| 5,315,990 A | 5/1994 | Mondry | |
| 5,337,743 A | 8/1994 | Repperger et al. | |
| 5,365,922 A | 11/1994 | Raemer | |
| 5,372,134 A * | 12/1994 | Richardson ................. | 600/323 |
| 5,590,852 A | 1/1997 | Olson | |
| 5,682,877 A * | 11/1997 | Mondry ................. | 128/204.23 |
| 5,791,982 A * | 8/1998 | Curry et al. .................. | 454/74 |
| 5,809,999 A | 9/1998 | Lang | |
| 6,117,073 A * | 9/2000 | Jones et al. ................. | 600/300 |
| 6,142,149 A | 11/2000 | Steen | |

(Continued)

OTHER PUBLICATIONS

"Mixed Venous Oxygen Saturation in Critical Care"—by John D. Conroy, Jr., and Jane Kirker-Conroy; Osteopathic Medical News, vol. IV, No. 2, pp. 18-19, 37-38, 43.

Primary Examiner—Justine R. Yu
Assistant Examiner—Annette Dixon
(74) Attorney, Agent, or Firm—McNees Wallace & Nurick LLC

(57) ABSTRACT

A noninvasive system for monitoring the oxygen saturation level of a person subjected to reduced atmospheric pressure for avoiding hypoxemia. The system monitors a person's oxygen saturation level, comparing the saturation level to a predetermined level. When the measured saturation level is less than the predetermined level, the person is then supplied with an oxygen mixture for increasing the subject's oxygen saturation level to a safe level. The person's exposed reduced atmospheric pressure is also compared with a predetermined range of pressure levels. If this predetermined range of pressure levels is exceeded or maintained for a predetermined time duration, the person is then supplied with an oxygen mixture. Additionally, a device is provided for performing oxygen flight planning calculations for estimating oxygen usage for a predetermined flight plan that is based on the above system.

16 Claims, 21 Drawing Sheets

OXYGEN DISSOCIATION CURVE

U.S. PATENT DOCUMENTS

| | | | |
|---|---|---|---|
| 6,244,540 B1 * | 6/2001 | Stabile et al. | 244/118.5 |
| 6,452,510 B1 * | 9/2002 | Zysko | 340/970 |
| 6,470,885 B1 | 10/2002 | Blue et al. | |
| 6,488,634 B1 * | 12/2002 | Rapoport et al. | 600/538 |
| 6,629,525 B2 * | 10/2003 | Hill et al. | 128/202.26 |
| 2002/0139368 A1 | 10/2002 | Bachinski | |
| 2002/0148470 A1 | 10/2002 | Blue et al. | |
| 2006/0213519 A1 * | 9/2006 | Schmidt et al. | 128/204.23 |

* cited by examiner

OXYGEN DISSOCIATION CURVE

US 7,246,620 B2

SYSTEM FOR MONITORING PILOT AND/OR PASSENGER OXYGEN SATURATION LEVELS AND ESTIMATING OXYGEN USAGE REQUIREMENTS

CROSS REFERENCE TO RELATED APPLICATIONS

This application is a continuation-in-part of application Ser. No. 10/419,672 filed on Apr. 21, 2003.

FIELD OF THE INVENTION

This invention relates to a system for monitoring oxygen saturation levels of and estimating oxygen usage requirements for aircraft passengers and crew, and more particularly, to avoiding hypoxemia in aircraft passengers and crew traveling in high performance unpressurized aircraft by monitoring oxygen saturation levels of and estimating oxygen usage requirements for the passengers and crew.

BACKGROUND OF THE INVENTION

Ascent to altitude by use of airborne craft was initially achieved by hot air balloon. The first passengers carried beneath the Mongolfier brothers balloon during a 1782 flight were a duck, a rooster and a sheep, as the effects of flight for a person were unknown. At least one hundred years later, the physiological effects due to unpressurized high altitude flying remained largely unknown. In 1875, a three man balloon crew first employed a supplemental oxygen source consisting of three goatskin bags connected to a centered wash bottle providing 72 percent oxygen totaling 440 liters. The balloon flight reached 28,000 feet in altitude. While attempting to conserve oxygen during the flight, the three men were overcome by a euphoric torpor induced by lack of oxygen, resulting in the deaths of two of the men. The survivor later recorded that when convinced of the need of oxygen, he was powerless to raise his arms, unable to raise the mouthpiece of the oxygen container to his lips, and though within easy reach, the oxygen which would have saved the lives of his companions went unused. An insufficiency of oxygen in the blood is defined as hypoxemia, while an insufficiency of oxygen in the body tissue is defined as hypoxia.

To address the adverse effects of in-flight oxygen deficiency, oxygen distribution systems were incorporated into aircraft. Pre-World War II pipe stem oxygen distribution systems were later replaced by pressure clearance systems at the end of the conflict. Soon after, constant flow masks were made available in general aviation. While initial commercial air transport in the United States in the 1930's did not raise a significant risk of hypoxia because of low flight altitudes, by the 1940's to 1960's, the service ceiling of commercial aircraft was at 40,000.

Each person has a different oxygen requirement and adaptation to altitude, and those requirements change on a daily, or more accurately, an hourly basis based upon fatigue, diet, hydration level, stress and other personal factors. Increases in altitude likewise increase the associated adverse effects, including changes in visual acuity, psychomotor performance and situational awareness. As altitudes increase above 10,000 feet and critically above 15,000 feet, the time of useful consciousness (TUC) decreases at 15,000 feet to 15-20 minutes. As expected, there is a difference in the physical fitness standards between commercial/military pilots and general aviation pilots and passengers.

The Federal Aviation Administration (FAA), mindful of the adverse effects to passengers and crew of aircraft operating at altitude, has developed regulations concerning the availability and use of sustenance and supplemental breathing oxygen. These regulations are divided into the following classifications: air transport, on-demand operations and general aviation. The regulations relating to general aviation are discussed herein. The term "passengers" or "occupants" as used herein may also include the pilot and crew of the aircraft. The term "subject" as used herein may refer to any person in the aircraft. The current regulations are based on rules initially established by empirical data and experience of the Civil Aviation Administration (CAA).

Requirements for general aviation supplemental oxygen is provided in 14 CFR 91.211 as cited in the Federal Register dated Aug. 23, 2001. While this regulation provides for aircraft having pressurized and unpressurized cabins, most of the single engine piston powered general aviation aircraft used under Part 91 of the regulations employ unpressurized cabins, which is the primary focus herein. 14 CFR 91.211 provides that supplemental oxygen shall be provided to a required minimum flight crew above cabin pressure altitudes of 12,500 feet, mean sea level (MSL), up to and including 14,000 feet MSL if the duration of the flight at that altitude is more than 30 minutes. Cabin pressure altitude is calculated by taking a pressure measurement inside the aircraft cabin and converting that pressure to an altitude, preferably by a device that performs this calculation automatically. At cabin pressure altitudes above 14,000 feet MSL, the required flight crew must be provided with and use supplemental oxygen. MSL altitude is the atmospheric pressure either directly measured by weather stations at sea level or empirically determined from the weather station pressure and temperature readings collected by weather stations not at sea level. At cabin pressure altitudes above 15,000 feet MSL, supplemental oxygen must be provided to each occupant of the aircraft. In other words, FAA regulations do not require providing supplemental oxygen to occupants (passenger that are not required flight crew) below 15,000 feet MSL.

It is noted that other FAA regulations under Title 14, such as Parts 121 and 135, relate to air transport and on-demand operations, which specify different, more stringent altitude requirements with respect to supplemental oxygen use for pilots. In other words, the altitudes triggering the requirements for supplemental oxygen are greater for general aviation use. For example, 14 CFR 135.89 provides that the minimum altitude is 10,000 feet MSL instead of 12,500 feet MSL for the pilot or flight crew. The time for the required crew to use supplemental oxygen is the same 30 minute duration. As a result, many pilots may be lulled into believing that the time they spend at higher altitude is of little concern and to "push the envelope," accepting higher altitudes when filing flight plans or maximizing the operational capabilities of their turbocharged piston powered engines without the use of supplemental oxygen. This misguided thinking has often concluded tragically. Flying at altitudes as low as 5,000 feet can affect certain individuals, particularly at night. It is estimated that pilot error is the primary cause of about 74 percent of all general aviation accidents. To understand how the present invention utilizes generally accepted clinical standards for hypoxemia, which can be easily and reliably determined and applied to help prevent hypoxia, a brief summary of human oxygen physiology is provided below.

Oxygen that is inspired through the mouth or nose proceeds down the trachea and into the main bronchi, flowing out into primary and secondary bronchi and then into the alveolar air units. The space between the mouth and the alveolar units is "dead space" because there is no air exchange in these tubes. In other words, that portion of air previously inspired only reaching this dead space retains its oxygen content and may again be inspired for air exchange. Oxygen and carbon dioxide exchanged in the alveolus is dependent on the diffusion capacity, which can be affected by age and chronic disease.

Ventilation and oxygen supplied for aerobic cellular respiration, is accomplished in the alveolar units which diffuses oxygen across the pulmonary membrane into capillary beds, the diffused oxygen in the alveolar units passing through the pulmonary cells into the pulmonary venules then into the pulmonary vein. Pressurized carbon dioxide ($PCO_2$) from the body flows from the pulmonary artery into the capillaries, then to the alveolar unit, where it similarly diffuses through the pulmonary membrane and is expired as a waste gas. The volume of air moved through the pulmonary units is known as minute ventilation with vital capacity being the total volume of the lung.

The actual air that we breathe is a combination of different gases at various pressures P. The pressure of oxygen ($PO_2$) is 159.1 torr in dry air, 149.2 torr in moist tracheal air at 37° C., 104 torr in the alveolar gas unit, 100 torr in arterial blood and 40 torr in mixed venous blood out of a total 760 torr at standard conditions. Thus, $PO_2$ as used herein may be defined to refer to the oxygen pressure level corresponding to ambient, tracheal or alveolar as appropriate to apply or calculate other physiologic parameters. In addition to $PO_2$, the partial pressures of $CO_2$ and $H_2O$ and $N_2$ are necessary to calculate the total and partial pressures of gases acting on the pilot (FIG. 5). The term torr refers to the pressure required to support a column of mercury 1 mm high under standard conditions, that is, standard density of mercury and standard acceleration of gravity. These conditions are at 0° C. and 45° latitude with acceleration of gravity is 980.6 cm/sec$^2$, torr is a synonym for "mm/Hg". An important constant to remember is the partial pressure of water vapor, for the trachea will always have a $PH_2O$ of 47 torr as inspired air will be saturated with water vapor as soon as it is inspired. Therefore only 760 torr-47 torr or 713 torr of pressure is available for the sum of pressures of oxygen, carbon dioxide and nitrogen at standard conditions of 0° C. and 45° latitude. Water vapor pressures increase with temperature, for example 20° C. has $PH_2O$ of 17.5 torr while 37° C. has $PH_2O$ of 47 torr. The $PO_2$ of moist inspired air in the trachea is actually 149 torr, which is 20.93% of 713 torr. While the trachea will always have a $PH_2O$ of 47 torr, what of the environment from which the inspired gases are drawn into the airway of the pilot of an unpressurized aircraft at 10,000 feet MSL? As the aircraft climbs, the partial pressure of $O_2$ and the temperature will fall with increasing altitude. Although air vents of the aircraft cabin are open to the cooler outside environment at increased altitude, typically the aircraft cabin air that is inspired by the aircraft passengers is heated and maintained at an elevated temperature for passenger comfort. Concomitantly, the ground barometric pressure and temperature will change as the aircraft navigates a course. These changes alter the baseline assumptions in actual partial pressure of gases at the indicated altitudes (IA) of the aircraft. In a pressurized aircraft such as a commercial transport aircraft pressurized at 4,000-8,000 feet MSL, a constant cabin temperature and a cabin pressure can be maintained. Over the time of a cross-country flight with decreased cabin pressure, the pilot and passenger(s) will notice lower extremity edema from lower cabin pressure relative to sea level.

For purposes herein, the pilot lung alveolar gas compartment is a critical volume. During respiration pilots expire $CO_2$ and absorb $O_2$ gases. The quantity ($CO_2$ ml excreted/ml $O_2$ absorbed) is the respiratory ratio R which gives a mean estimate of $PO_2$ and $PCO_2$ over time. The mean alveolar $O_2$ ($PAO_2$) at sea level and 37° C., is defined in equation 1

$$PAO_2 = FIO_2(713) - PACO_2\left[FIO_2 + \frac{1-FIO_2}{R}\right] \quad [1]$$

where $FIO_2$ is the fraction of inspired $O_2$ (percent), and $PACO_2$ is the mean alveolar $CO_2$. Recall that the total pressure of all alveolar gases at sea level is 760 torr. Pilot lung volumes and actual cabin altitudes will be discussed in additional detail below. As the altitude increases, the $FIO_2$ remains relatively constant at 21%, the $PAO_2$ decreases as the barometric pressure decreases with altitude (at 18,000 feet MSL; 50% of atmospheric pressure at sea level is absent). Therefore, the partial pressures of all gases decrease with increasing altitude. As hypoxemia is defined as the lack of adequate oxygen supply in the blood, individual pilot hypoxemia can occur at an altitude where the oxygen supply for the individual pilot is inadequate for the pilot physiologic oxygen demand. The key factor is not a specific aircraft altitude MSL but rather the oxygen demand of the pilot. The diffusion capacity of the gases varies with the individual, dependent on the current status of the health of the pilot's lung alveolus. The oxygen diffuses from the alveolus to the venue capillary into the blood serum and then is absorbed by the red cell and stored there for transport in the body.

The components of the oxygen transport system are comprised of cardiac output of the heart (CO), the hemoglobin concentration of the blood (Hb), oxygen red cell saturation of the red blood cells ($SAO_2$) for arterial circulation, ($SVO_2$) for venous circulation, and the oxygen consumption of the body ($VO_2$). Oxygen saturation is defined as the percentage of oxygen bound hemoglobin to the total amount of hemoglobin available. Oxygen saturation in the blood may be measured by a co-oximeter in the pulmonary laboratory.

Invasive medical oxygen moniters or oximeters, such as those originally manufactured by Oximetrix Inc., of Mountain View, Calif., may include a catheter, an optical module and a digital processor. The catheter, such as a pulmonary artery catheter typically includes a balloon on a distal tip for flow-directed placement, and a proximal lumen, which is a thermistor similar to a standard pulmonary artery thermodilution catheter, and two optical fibers. One fiber transmits light from the optical module to the distal tip of the catheter while the second fiber returns the reflected light from the distal tip back to the optical module. The Oximetrix optical module contains three light emitting diodes (LED's) that illuminate, via one optical fiber, the blood flowing past the catheter tip. Light reflected from the blood is returned through the second fiber and directed into a solid state photodiode detector within the optical module. The module converts the light intensity levels into electrical signals for transmission to the processor. The digital processor computes percent of oxygen saturation values based on the electrical signals transmitted and received from the optical module. These values are continuously displayed in numerical form by LED and are recorded by the processor's built-in strip recorder. Later models have LED display only but functionally are the same unit.

Oximeters have been used under clinical conditions, especially for monitoring oxygen saturation levels of critically ill patients. However, catheters, such as Opticath® catheters which are used with Oximetrix oxygen monitors, are invasive as the catheter must be inserted inside the pulmonary artery. Alternately, oxygen saturation may also be measured transcutaneously using infrared light in pulse oximetry units. Pulse oximeters similarly employ an LED and photosensor placed on opposite sides of arterioles located in a subject's tissue that can be transilluminated. In other words, pulse oximeters may be positioned over a narrow portion of a subject's anatomy, such as a finger or ear lobe. Typically, the pulse oximeter "clips" over opposed sides of the end of an appendage, such as an index finger. Pulse oximeters have many advantages over Opticath® catheters. They are noninvasive, as the subject's skin is not pierced, require no calibration, provide nearly instantaneous readings, rarely provide false negative information, require no routine maintenance, and are relatively inexpensive to purchase. These units are accurate in normal physiologic states, although in clinical situations of hypoprofusion and hypothermia the transcutaneous oxygen saturation measurements are inaccurate. Oxygen saturation measured in a pulmonary artery by either direct blood measurement (blood gas studies) or fiber-optic pulmonary artery catheter (co-oximetry) or pulse oximetry is generally accurate within 2% of the actual value.

Co-oximetry and pulse oximetry provide measurements of hemoglobin saturation. Molecular oxygen is carried within the hemoglobin molecule to tissues in the body, the oxygen carrying capacity possibly varying over time in response to changing health and/or environmental conditions. Normal hemoglobin carries 98% of the oxygen within the hemoglobin molecule with approximately 2% of the oxygen in the blood serum. This, however, can change significantly in diseases such as sickle-cell anemia (HbSS>50%) in which there is abnormal sickling of the hemoglobin molecule and decrease in oxygen carrying capability. This can be aggravated in periods of hypotension and dehydration even in sickle cell trait (HbSS<50%). Oxygen transport ($O_2T$) occurs best at hemoglobin values of 40-43%. At hematocrit values greater than 50%, the result is increased viscosity and sluggishness of the blood, whereas hematocrit values less than 40% have the result of decreased hemoglobin and therefore less molecular oxygen saturation, a result of anemia. Oxygen content relates to the ability of the subject to adjust to physiologic stress.

The driving force in the oxygen transport system is the heart and resultant cardiac output (CO). The cardiac output is typically about 5.0 liters per minute, with maximums up to about 15.0 liters per minute during exercise. However, cardiac output can drastically fall to about 1.0 or 2.0 liters per minute in states of heart failure. In normal hemostasis with normal hemoglobin cardiac output, and adequate oxygenation there should be sufficient oxygen content in the blood and this content will be transported to peripheral tissues for consumption. Provided below are some equations relating to the oxygen transport system.

Equations of the Oxygen Transport System

1. Oxygen Saturation (%)

$$SO_2 = \frac{HBO_2}{Hb + HBO_2} \times 100$$

Arterial ($SAO_2$) 91%–97%
Venous ($SVO_2$) 60%–75%
2. Oxygen Content ($CO_2$) (mL $O_2$/100 mL blood = vol %) arterial (2% $O_2$, dissolve) + (98%/$O_2$ Hb saturated)
Arterial
$CAO_2$ = ($PO_2$ × 0.0031) + (Hb × 1.38 × $SAO_2$)
$CAO_2$ = (100 torr × 0.0031) + (15 g × 1.38 × .97)
$CAO_2$ = .3 + 20.1
$CAO_2$ = 20.4 vol. %
Venous
$CVO_2$ = ($PVO_2$ × 0.0031) + (Hb × 1.38 × $SVO_2$)
$CVO_2$ = (40 torr × 0.0031) + (15 g × 1.38 × .75)
$CVO_2$ = .12 + 15.52
$CVO_2$ = 15.64 vol. %
3. Oxygen Transport ($O_2T$) (mL $O_2$ /min)
Arterial: $O_2TA = CO \times CAO_2 \times 10$
Venous: $O_2TV = CVO_2 \times 10$
4. Oxygen Consumption ($VO_2$) (mL $O_2$/min)
$VO_2 = CO \times Hb \times 1.38 (SAO_2 - SVO_2) \times 10$
$VO_2$ = 5 L/min × 15 g × 1.38 (.97 – .75) × 10
$VO_2$ = 228 mL/min
5. Cardiac Output (L/min)

$$CO = \frac{VO_2}{CAO_2 - CVO_2}$$

LIST OF ABBREVIATIONS $PVO_2$=mixed venous oxygen mm Hg (31-40) (torr)
$PO_2$=arterial oxygen tension mm Hg (60-100) (torr)
P50=partial pressure mm Hg of oxygen at 50% saturation of hemoglobin molecule (26.6 torr)
Hb=hemoglobin (g/dL)
Hct=hematocrit (%)
ODC=oxygen dissociation curve
$CVO_2$=venous oxygen content mL $O_2$/100 mL blood
$CAO_2$=arterial oxygen content mL $O_2$/100 mL blood
$VO_2$=oxygen consumption
CI=cardiac index (1/min/SA)
CO=cardiac output (1/min)
$SAO_2$=arterial oxygen saturation (91-97) (%)
$SVO_2$=mixed venous oxygen saturation (60-75) (%)
$SO_2$=oxygen saturation
$O_2TA$=oxygen transport (arterial)
$O_2TV$=oxygen transport (venous)
0.0031=diffusing capacity coefficent of plasma $O_2$
1.38=mL of $O_2$ per gram of hemoglobin
10=conversion factor to mL/100 mL blood Oxygen saturation is determined by the biochemistry of the red blood cell, factors such as 2-3-DPG, red cell pH and temperature, and actual hemoglobin values can be plotted in oxygen pressure torr versus oxygen saturation with a hemoglobin saturation curve, also referred as the oxygen disassociation curve (ODC), also referred as the hemoglobin disassociation curve, as illustrated in FIG. 1. P-50 is defined as 26.6 torr at 50% oxygen saturation. The ODC is affected by temperature, pH, hemoglobin value, 2-3-DPG, and ambient temperature and pressure (ATP) levels. These factors all affect erythrocytic functions and compensate for variation in body homostasis. In hyperventilation, the increased flow of oxygen results in acidic blood serum levels (lower pH), higher body temperature and higher 2-3-DPG environments. Corresponding oxygen unloading results in alkaline blood serum levels (higher pH), lower body temperature, and lower 2-3-DPG levels. A decrease in hemoglobin would decrease the overall ODC curve. In essence, the respiratory function of the hemoglobin molecule is similar to the respiratory function of the lung. On the ODC curve the oxygen saturation value is between about 91% and about 97%, corresponding to oxygen torr between about 60% and 100%. While there is a wide gradient of torr, there is a small difference in oxygen saturation in oxygen returning to the heart, venous $SVO_2$. Referring to FIG. 1, normal $SVO_2$ values of 60-75% saturation correspond to a range of 31-40 torr. The mixed venous oxygen saturation of blood at the right atrium in the heart would not be measured in flight, however, oxygen saturation by pulse oximetry can easily be measured in flight.

The P50, the value of serum $PO_2$ torr at 50% Hb saturation can be affected by temperature, as defined by equation 2

$$P50_T = 26.6 \times 10^{(6.024(T-37))} \quad T = \text{temp } ° C. \text{ Pilot} \qquad [2]$$

or by acid base balance in terms of pH, as defined by equation 3

$$P50_{PH} = 26.6 \times 10^{(0.48(pH-7.4))} \qquad [3]$$

where $$pH = 6.10 + \text{Log} \frac{[HCO_3]}{[6.030/PCO_2]}$$

and these values will shift the hemoglobular disassociation curve (ODC) right (higher temperature or lower pH) or left (lower temperature and higher pH). A left shifted curve increases P50 and $O_2$ saturation.

The ODC can be calculated by the Aberman technique provided in equation 4 where:

$$\text{ODC } O_2 \text{ Sat} = \sum_{I=0}^{I=7} K_I + I(PO_2 - 27.5)/(PO_2 + 27.5)^I \qquad [4]$$

and estimates of oxygen need can be calculated with measured $SAO_2$ and expired $CO_2$ ($ECO_2$). The ODC changes with anemia giving a flatter curve. In certain circumstances a crossover P50 can occur where the normal physiologic response to improved $O_2$ delivery actually can worsen the $O_2$ content.

Acclimatization includes an increased respiration and cardiac output due to the hypoxic stimulation, and the function of both carotid and aortic body receptors. In addition, there is increased diffusion of oxygen and carbon dioxide through the alveolar membranes, the result of rising capillary blood volume, increased lung volume, and a rise in the pulmonary artery pressure. Over the long term, polycythemia will increase the blood hemoglobin from stimulation of the bone marrow by erythropoetin (EPO) which is secreted by the kidney. The degree of polycythemia is adversely related to the degree of oxygen saturation. This adjustment requires two to three weeks of erythropoetin stimulation to increase the hemoglobin volume and the hemoglobin will increase to a polycythemic level. In addition, increased vascularity of the capillary membrane may result from long term hypoxemia and there may be changes in cellular oxidative metabolism, making it a struggle to survive in a more hypoxemic environment. On the hemoglobin disassociation curve, there would be a decreased affinity of hemoglobin for oxygen resulting in increased production of 2-3-DPG within red blood cells. 2-3-DPG, which is short for 2-3-diphosphoglycerate, is an organic phosphate that helps oxygen to combine with red blood cells, resulting in an increase in the number of red blood cells. The resultant left shift in the ODC curve improves off-loading of the oxygen to tissues by as much as 10-20% at 15,000 feet. However at higher altitudes this off-loading is a detriment. The resulting respiratory alkalosis is compensated by the kidney in retaining ammonium ions and secreting large amounts of bicarbonate. The slow process may take days to manifest itself in its compensatory mechanism. With hyperventilation, however, by increasing minute ventilation to the lung or increased oxygen, overall oxygen content to the lung will decrease the $PCO_2$ content. However, two important events known as hypocapnia with alkalosis are the result of hyperventilation. This is a result of lowering alveolar blood carbon $PCO_2$ below normal hypocapnia, and the acid/base balance being disturbed, becoming more alkalotic with the result of alkalosis. Measurement of expired $CO_2$ ($ECO_2$) of the pilot will assist in defining acid/base status (pH).

The use of supplemental oxygen to improve oxygen tension and hemoglobin saturation in the blood and decrease the risk of hypoxemia can be associated with oxygen toxicity. In the medical setting mechanical ventilation with 100% inspired oxygen tension can lead to pulmonary toxicity and concomitant pulmonary fibrosis in relatively short periods of time and is a considerable risk in the use of high-dose oxygen in acute medical care. Prolonged breathing of 60-100% oxygen for more than 12 hours will irritate the pulmonary passages, resulting in the Lorraine-Smith effect which is a combination of cough and congestion, sore throat and substernal soreness. After 12 hours, decreased vital capacity occurs which is accompanied by severe pulmonary damage. At greater oxygen tensions, such as hyperbaric oxygen tensions or tensions in which positive end-expiratory pressure ensues, this pulmonary toxicity can be significant and cause sufficient damage in the lungs to offset the benefit of mechanical ventilation with oxygen support. However, oxygen utilization in general aviation for short periods of time, even at 100% oxygen levels, would be expected to have minimal, if any, oxygen toxicity on the subject. Many flights requiring oxygen in an unpressurized aircraft up to 25,000 feet will be limited by the fuel supply and total payload of the aircraft with current payloads of 1,000 to 2,000 pounds when calculating weight and balance for fuel, passengers, and baggage, the flight envelope would be well less than four hours of which only three hours may be under actual oxygen use because of limitation of oxygen storage systems in the aircraft. However, the possibility of oxygen toxicity after daily use on multiple flights in a short timespan of days has not been studied.

Thus, general aviation, in which an unpressurized aircraft cabin may be subjected to altitudes up to about 25,000 feet, requires a thorough understanding of oxygen physiology. There is a decrease in human performance and that decrement starts at about 5,000 feet. Visual color perception decreases at this altitude, and is also manifested during night visual conditions. Interestingly, flying at altitude and scuba diving to great depth may produce similar physiological effects. Although the pressures exerted on the human body from each activity are on opposite extremes, that is, from small fractions of an atmosphere at flight altitude as measured at sea level to pressures approaching and even exceeding ten times the atmospheric pressure at sea level, i.e., when diving, 297 feet diving depth in sea water equals ten sea level atmospheres, the potential damage to the human body from sufficient exposure to either pressure extreme can be devastating.

Another matter arising in unpressurized aircraft cabins is the use of climate control, that is, heat, within the cabin. To maintain cabin temperatures that are comfortable to humans, unpressurized aircraft cabins are typically heated since air temperatures typically decrease two degrees Celsius (3.6° F.) for each 1,000 feet increase in altitude. The air can be of low humidity giving rise to a "high desert" environment causing dehydration. As stated previously, MSL altitude is the atmospheric pressure either directly measured by weather stations at sea level or empirically determined from the weather station pressure and temperature by weather stations not at sea level. However, this pressure fails to take into account the effect on the oxygen content inside the heated aircraft cabin, which due to its elevated temperature with respect to the outside air, equates to an even greater altitude than MSL altitude. In other words, by virtue of heating the cabin air that is maintained at substantially the same pressure as the air outside the cabin, the heated cabin air expanding as it is heated, a portion of the heated cabin air is vented from the fixed volume aircraft cabin. This venting further reduces the oxygen content within the aircraft cabin so that the effective cabin altitude, based on the actual content of oxygen remaining in the cabin, may be different than the (MSL) altitude measured based on cabin altitude pressure. Cabin density altitude takes into account temperature and pressure deviations inside the aircraft cabin.

Cabin density altitude may be derived from well defined relationships in gas laws. Altitude pressure ratio ($\delta$) equals the ambient static pressure (P) divided by the standard sea level static pressure ($P_o$) as shown in equation 5.

$$\delta = P/P_o \quad [5]$$

Temperature ratio ($\theta$) may be calculated by dividing the ambient air temperature (T) by the standard sea level air temperature ($T_o$) as shown in equation 6. These temperature units must be converted to absolute units, such as the Kelvin scale as shown in equation 7.

$$\theta = T/T_o; \quad [6]$$

$$\theta° K = (\theta°C. + 273)/298 \quad [7]$$

Density ratio ($\sigma$) may be calculated by dividing the ambient air density ($\rho$) by the standard sea level air density ($\rho_o$) as shown in equation 8.

$$\sigma = \rho/\rho_o; \quad [8]$$

Density ratio ($\sigma$) may also be defined as the altitude pressure ratio ($P/P_o$) divided by the temperature ratio ($T/T_o$) as shown in equation 9.

$$\rho/\rho_o = (P/P_o)/(T/T_o); \text{ substitution yields } \sigma = \delta/\theta \quad [9]$$

Pressure altitude ($P_B$) is the correction of altitude from standard conditions of barometric pressure of 29.92 in/Hg and 15° C., with "a" representing altitude in meters, as shown in equation 10

$$P_B = 760 \, (e^{-a/7924}) \quad [10]$$

and corrections of pressure altitude for temperature is density altitude (Hd) as shown in equation 11

$$Hd = 145539[1 - (\sigma)^{0.4699}] \quad [11]$$

where $\sigma$ is the atmospheric density ratio as discussed above.

Density altitude is typically calculated to determine aircraft performance.

Preferably, pressure altitude $P_B$ is calculated by utilizing equation 10 to make corrections both prior to and even during the flight as an altitude reference regarding the provision of supplemental oxygen to passengers. There is a relationship between pressure altitude and the alveolar oxygen tension pressure $PO_2$ that produces an arterial oxygen saturation value $SAO_2$ of about 91%, which corresponds to the physiologic value of increased risk of hypoxemia, that will be discussed in more detail below. For purposes herein, unless otherwise specified, all altitude references in terms of hypoxemia and ds91% saturation value, also referred to as ds91% alt, refer to pressure altitude, and references to atmospheric pressures or cabin altitude pressure are measured in terms of pressure altitude. Alternately, other altitudes, such as cabin density altitude which is density altitude as it relates to ambient cabin temperature versus outside air temperature (OAT), may also be calculated.

Applicant has found that each individual has a relatively narrow range of $PO_2$ values that will bring about hypoxemia in that individual. Although health factors previously discussed may cause the $PO_2$ value for a specific instance of time to be at either extreme of this range, research has indicated that this range appears to be repeatable, and therefore useful to calculate critical altitudes which under the certain temperature and pressure conditions present at the time of the flight significantly increases the risk of inducing hypoxemia for that individual. Armed with this knowledge, the pilot may choose to alter flight plans, or at least ensure that adequate on-board oxygen is provided the passengers. Short of the onset of an adverse medical condition, an individual's $PO_2$ level appears to change gradually over time so that once a few $PO_2$ readings have been taken, the individual's $PO_2$ level may not need to be so closely monitored.

Similarly, oxygen flight planning may be performed to estimate the amount of on-board oxygen that should be carried to avoid the onset of hypoxemia of passengers by applying the above equations and estimating certain passenger parameters if they are unavailable.

While many factors may significantly affect the human body's ability to process oxygen at a given moment even for the same individual, especially in a reduced oxygen environment, it is possible to measure the effects objectively against well known clinical standards for an increased risk of hypoxemia. Such a standard is the percentage of arterial oxygen saturation $SAO_2$ from the ODC curve previously discussed (FIG. 1). An $SAO_2$ value below about 91% (60 torr) is generally accepted as a clinical standard for an increased risk of hypoxemia, requiring immediate medical attention in the acute situation, typically providing the subject with a higher concentration of breathing oxygen, typically pure oxygen, to raise the subject's oxygen saturation value to a safe level above the hypoxemic level. It is recognized that hypoxemia may occur at a higher $SAO_2$ value than 91%, especially when an individual is subjected to a high $O_2$ demand situation. For example, most any type of severe physical injury, including, but not limited to, heart attack, gun shot, burns, or broken bones could result in bringing about the onset of hypoxemia of $SAO_2$ values in excess of 91%. Conversely, hypoxemia may not occur until $SAO_2$ values are less than 91%. However, absent exigent circumstances, which would already warrant increased medical attention, the clinical standard of about 91% is the preferred value.

There is a need in the art for a system for monitoring the oxygen level of a subject being exposed to reduced atmospheric pressure by a noninvasive device for measuring the oxygen saturation level of the subject so that by comparing that measured level with a predetermined oxygen saturation level, the subject may be offered enriched breathing oxygen to return the subject's oxygen saturation level to at least a second predetermined level before performance is adversely affected. Accurately monitoring the oxygen red cell blood saturation level of the subject may be an effective technique.

There is further a need in the art to estimate oxygen usage for all general aviation aircraft having either an unpressurized cabin or a pressurized cabin.

SUMMARY OF THE INVENTION

Applicant has found that there is a relationship between pressure altitude and the alveolar oxygen tension pressure $PO_2$ that produces an arterial oxygen saturation value $SAO_2$ of about 91%, which corresponds to an increased risk of hypoxemia in a person. That is, it has been found that a person having an $SAO_2$ value of about 91%, even for a brief period of time, is at increased risk for the possible onset of hypoxemia. Applicant has also found that each person has a unique pressure altitude corresponding to the increased risk of hypoxemia that typically remains substantially constant over at least short durations of time, and possibly extending to at least several months, and even years. As previously discussed, even short term changes in medical condition, such as hydration level or stress level, may affect the pressure altitude level corresponding to the increased risk of hypoxemia, as well as more gradual changes in medical well-being such as physical conditioning and aging. These discoveries form the basis for the present invention.

The present invention relates generally to a safety system for monitoring the oxygen saturation level of a subject being exposed to reduced atmospheric pressure and avoiding hypoxemia corresponding to a predetermined oxygen red cell saturation level for arterial/venous circulation. For purposes herein, unless otherwise specified, all references to altitude refer to pressure altitude, and references to atmospheric pressures or cabin altitude pressure are measured in terms of pressure altitude. The safety device system includes a noninvasive monitoring device usable by a subject to obtain at least one oxygen red cell saturation level measurement of the subject at reduced atmospheric pressure, the saturation level measurement being comparable to a predetermined oxygen saturation level. Upon the measured saturation level measuring less than the predetermined saturation level, the subject is then supplied with an oxygen mixture from a supplemental oxygen source for increasing the subject's oxygen saturation level to a second predetermined oxygen saturation level. Another portion of the safety system relates to comparing the subject's exposed reduced atmospheric pressure with at least one predetermined range of reduced atmospheric pressure levels. If the subject's exposed atmospheric pressure falls on or within the one predetermined range of reduced atmospheric pressure levels for a predetermined time duration or if the subject's exposed atmospheric pressure exceeds the one predetermined range, irrespective of the time duration, the subject is then supplied with an oxygen mixture from the oxygen source, or given an audible, visual or tactile sensation to respond to the warning.

The safety system of the present invention includes access to stored personalized data taken at cabin pressure altitudes from previous flights, but may also include other measured altitudes, such as density altitude or other stored altitude readings, that may be converted to signals prior to transmission to a logic device. The logic device is adapted to monitor all hardware associated with the safety system. The personalized data and logic device may be located in or remote from the aircraft in various embodiments of the safety system. A noninvasive body monitoring device for taking a physiological reading attached to each passenger and a pressure sensor located within the aircraft cabin take respective readings at substantially the same instant of time. These readings are provided to the logic device and may be converted to a digital signal, depending upon whether the components are located within the aircraft or remote to the aircraft, such as on the ground. Both the body monitor reading and the pressure reading are separately compared to predetermined standards in a body monitoring branch and a pressure monitoring branch of the safety system.

In the body monitoring branch, the body monitor reading is compared with a predetermined physiological standard associated with hypoxemia. If the body monitor reading meets this standard, the body monitor/pressure data may optionally be transmitted to the data storage device in preparation of taking the next body monitor/pressure reading. However, if the body monitor reading fails to meet the predetermined standard, possibly subject to confirmation readings, a first warning message from a warning device is activated, providing any combination of an audible, visual or tactile sensation to respond to the warning, and supplemental oxygen is provided to at least the passenger having the sub-standard body monitor reading. The body monitor/pressure reading for that passenger is preferably transmitted to data storage.

In the pressure monitoring branch, the stored personal flight data provides the first measuring standard. That is, for each passenger the stored altitude portion of this data corresponding to a sub-standard body monitor reading taken during a previous flight is employed as a comparative standard against the current aircraft pressure altitude. If the current aircraft pressure altitude is greater than any of the stored "personal altitudes," a third warning message from the warning device is activated to alert both the passenger and pilot, if they aren't the same person. However, no supplemental oxygen is dispensed if all passengers maintain body monitor readings exceeding the predetermined standard. The cabin pressure altitude is also compared to 12,500 feet MSL altitude. If the cabin pressure altitude exceeds 12,500 feet MSL, a second recorded time reference is initiated to correspond to the amount of time the aircraft is at or greater than 12,500 feet MSL. If the second recorded time reference at an altitude equal to or above 12,500 feet MSL meets or exceeds 30 minutes, a fourth warning message from the warning device is activated and supplemental oxygen is made available for each passenger, which is in compliance with current FAA regulations. Alternately, without breaching the 30 minute duration at or above 12,500 feet MSL, if 14,000 feet MSL is exceeded, supplemental oxygen is likewise dispensed to all passengers to further comply with current FAA regulations. In fact, the process of the present invention is much more stringent than current FAA regulations in that the current FAA regulations provide that only above 15,000 feet MSL must supplemental oxygen be made available to all passengers. Below 15,000 feet MSL, supplemental oxygen must only be made available to the required flight crew. Further, cabin pressure altitudes, which are much more stringent than the FAA regulations, may be calculated and employed in place of the FAA regulations.

In one system embodiment, all hardware associated with the safety system may be portable. That is, the safety system which is incorporated within a single portable container, with the exception of the monitoring device, may be brought on board the aircraft for use during the flight and removed from the aircraft upon completion of the flight, and may be further dedicated for the use of a particular passenger.

The stored personal data, which represents flight history information for a particular passenger, may be advantageously used to alert the passenger and pilot of cabin pressure altitudes associated with reduced blood saturation values. If the cabin pressure altitude of the current flight is equal to or exceeds the stored data altitude level, the third warning message from the warning device secured within the portable container, such as an audio message possibly accompanied by a visual display on the monitoring device may be repeated at predetermined time or increased altitude increments. This past data is a valuable precautionary criterion for establishing heightened awareness of hypoxemic conditions and preventing potential catastrophic results.

A body monitor, such as a pulse oximeter, is noninvasively secured to the passenger as previously described. Employing an LED and photosensor placed on opposite sides of an artery located in the passenger's tissue, the passenger tissue is transilluminated, the reduced amount of illumination that is sensed by the photosensor corresponding to a saturation level in the blood that is calculable by the logic device. A cumulative timing device associated with the logic device may then be initiated. The purpose of the cumulative time measurements is to permit, if desired, a convenient means to determine the time differential between any two data readings or even between first and/or second recorded time references, since the first and second recorded time references may be periodically reset. At substantially the same instant in time, as controlled by the logic device, a pressure sensor provides an output, typically a voltage, in response to the pressure level in the aircraft cabin. Each of these analog signals is then transmitted to the logic device for further processing. Alternatively, these signals may be further converted by an analog-digital converter to a digital signal or word prior to transmission to the logic device.

The logic device starts the body monitoring branch of the safety system, comparing the passenger's blood saturation level measurement against a generally accepted clinical standard for an increased risk of hypoxemia, about 91% arterial blood saturation, $SAO_2$. If the passenger's blood saturation level fails to meet this standard, possibly subject to confirmation by subsequent measurements, a first warning message from the warning device is initiated. As the first warning message is initiated, a supplemental on board source of breathing oxygen is promptly provided to the passenger. The current data readings, which contain both a signal corresponding to a cabin pressure altitude reading and a signal corresponding to a sub-par (below about 91% $SAO_2$) blood oxygen saturation level, may then be transmitted to the memory device for storage of the information.

The present invention also relates generally to a device for performing oxygen flight planning calculations for estimating oxygen usage for a predetermined flight plan. The estimated oxygen usage is based on monitoring the oxygen saturation level of a subject being exposed to reduced atmospheric pressure and avoiding hypoxemia corresponding to a predetermined oxygen red cell saturation level for arterial/venous circulation. The device makes use of information gathered from previous flights, if available, to estimate when oxygen will need to be supplied to a passenger. That is, when the proposed flight plan is at a cabin pressure altitude that has corresponded to an $SAO_2$ value below about 91% for a passenger, oxygen is allocated to that passenger for the duration of time the aircraft is at that cabin pressure altitude. The device permits oxygen planning for multiple passengers. If the passengers have not flown, the device estimates certain parameters, based on factors such as age, gender, height and weight and overall health, or the user may simply select a flight parameter, such as cabin pressure altitude, or alternately, other available altitudes. As the passenger flies additional times, his personal flight data is updated to supplement previous information.

The device may resemble a conventional flight calculator, such as a hand-held EB-6 military flight calculator, which includes an input device for inputting information into the device, such as a keypad, and an output device, such as a display. The device has two modes of operation. In a first mode, the user may input known flight parameters, such as ambient temperature, pressure, the temperature at an intended flight altitude, and then query the device to determine which flight parameters may be calculated based on the known parameters provided. Upon selecting the available flight parameters displayed, the device calculates and outputs the calculated flight parameters to the output device.

In a second mode, the user may select flight parameters of interest, followed by the user inputting known flight parameters. The device then prompts the user for missing parameters required to calculate the flight parameters of interest, either permitting the user to provide or estimate the values of the missing parameters, or alternately, providing estimated default values so that values for the flight parameters of interest may be calculated. Both modes of operation further have the capability of updating the estimated oxygen requirements for a flight, even as the flight is taking place, as flight conditions such as atmospheric conditions affecting the desired cabin pressure altitude may change, or if one or more of the passengers begin requiring oxygen at a lower altitude than previously expected. Further, the device may be configured to automatically receive and calculate flight parameters, including recognition of oxygen dispensing systems installed in the using aircraft to automatically incorporate the appropriate dispensing system.

The present invention contemplates this safety device system for use in all general aviation aircraft having either an unpressurized cabin, or a pressurized cabin.

A principal advantage of the present invention is the provision of a system utilizing a consistent, generally accepted and applicable clinical standard for monitoring by reliable, noninvasive means against the onset of hypoxemia. The noninvasive means permits the in-flight use of this system for pilots, crew and/or passengers of unpressurized general aviation aircraft.

Another principal advantage of the present invention is the provision of a device for performing oxygen flight planning calculations for estimating oxygen usage for a predetermined flight plan which employs a reliable, noninvasive monitoring system against the onset of hypoxemia.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible, the same reference numbers will be used throughout the drawings to refer to the same or like parts.

DETAILED DESCRIPTION OF THE INVENTION

Figure 1:
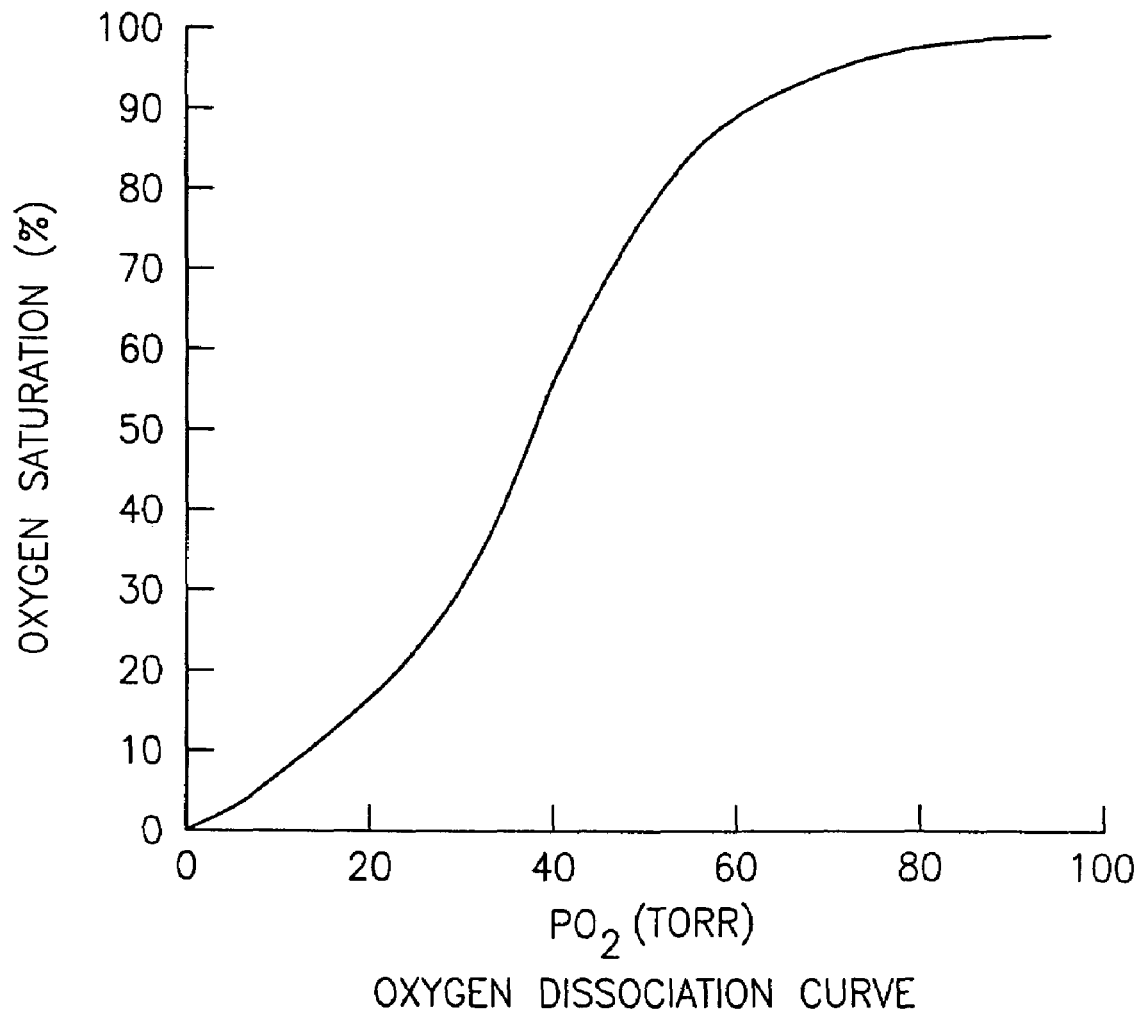
FIG. 1 is a graph illustrating an oxygen disassociation curve (ODC).
Figure 2A:
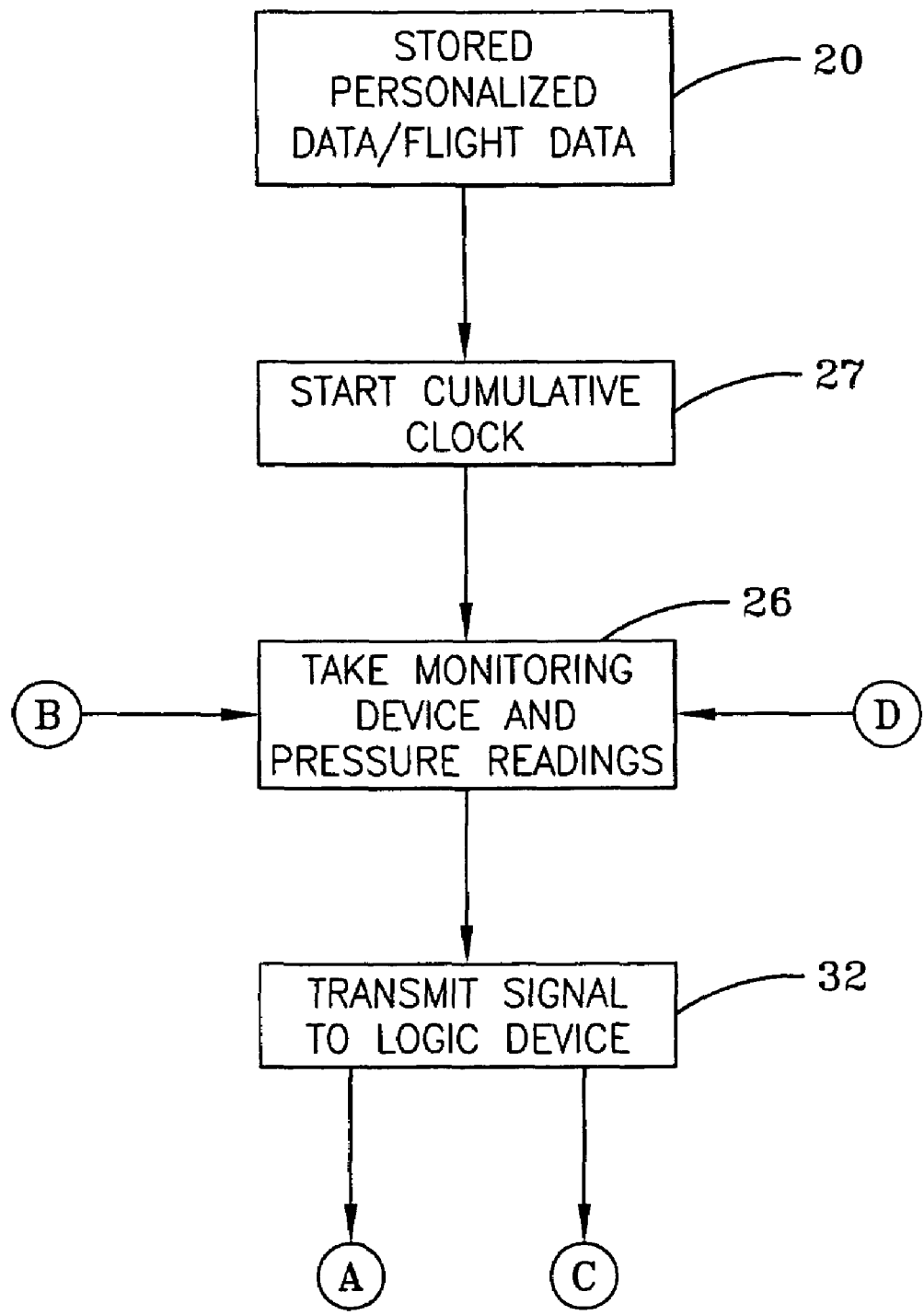
FIGS. 2A-2C are process diagrams corresponding with the operation of the system of the present invention.
Figure 2B:
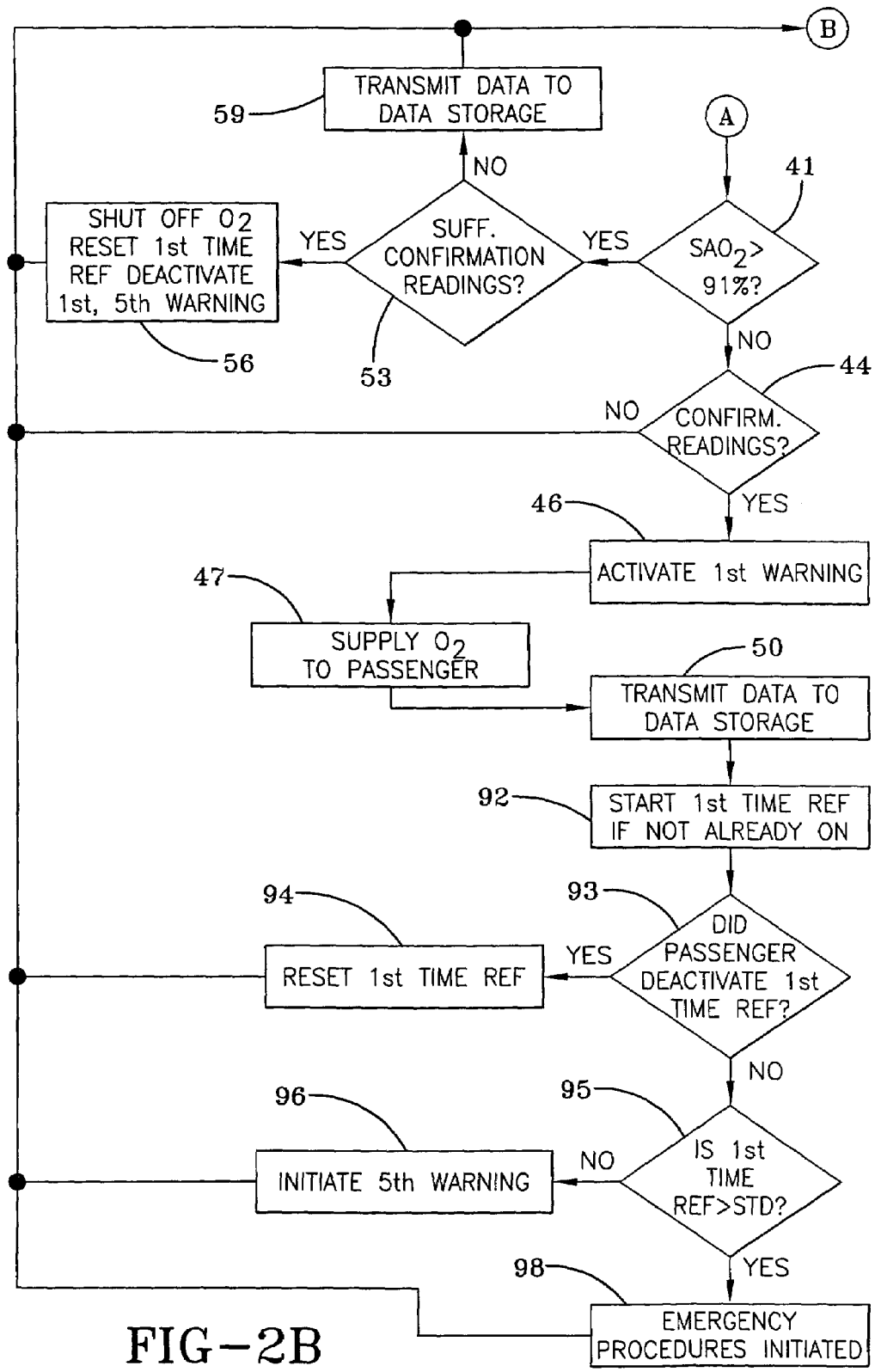
Figure 2C:
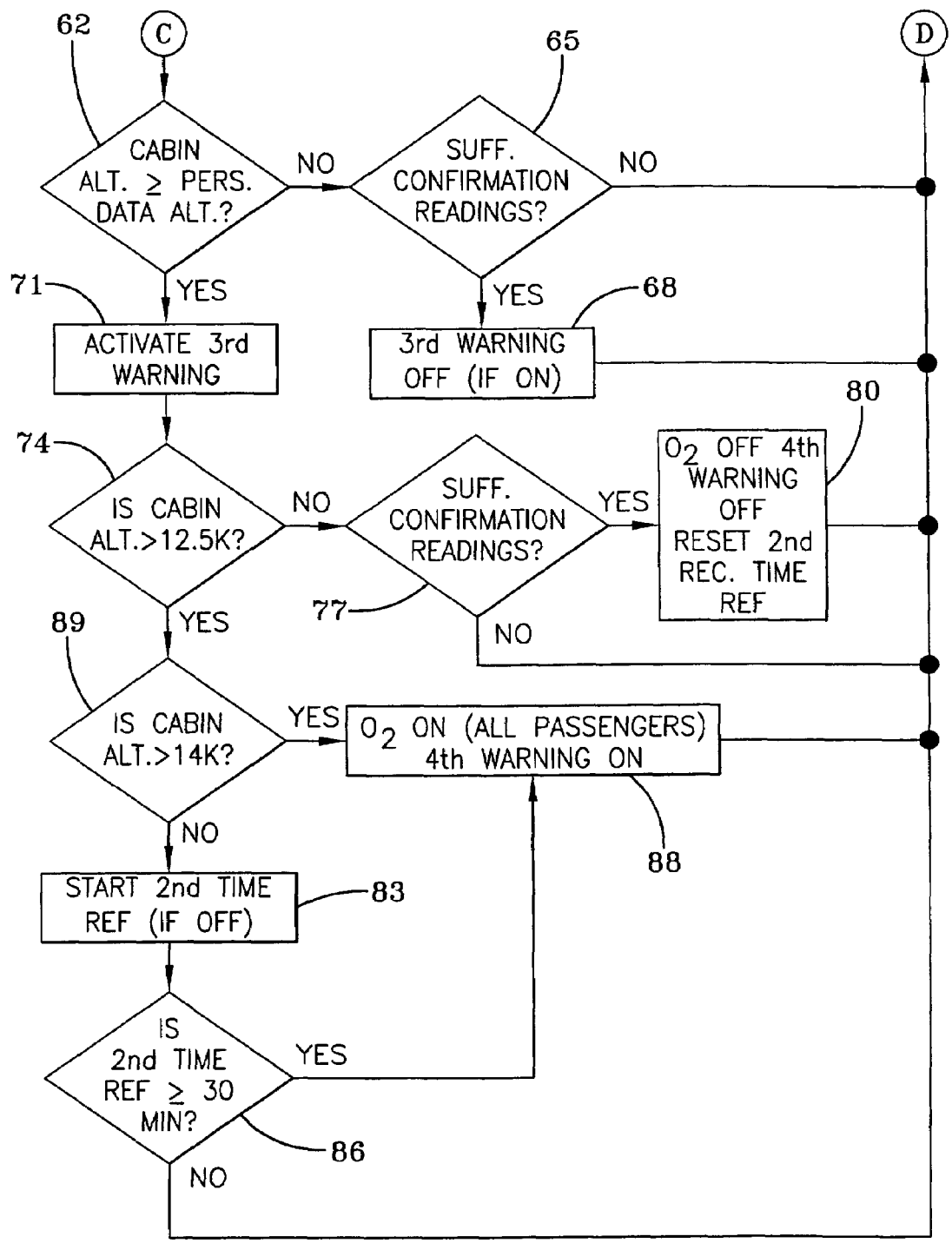
Figure 6:
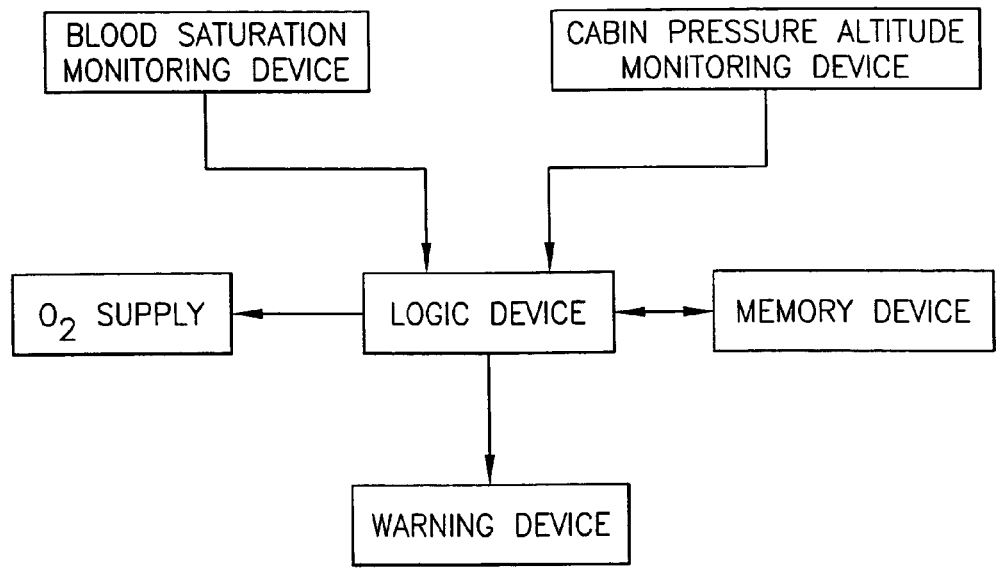
FIG. 6 is a general schematic illustrating the components of the system of the present invention.

The present invention includes a process, referring to FIGS. 2A-2C, for monitoring the oxygen red blood saturation level for arterial circulation, $SAO_2$, of a subject exposed to reduced atmospheric pressure levels, such as unpressurized aircraft cabins, to avoid safety hazards associated with hypoxemia. FIG. 6 is a general schematic of the system implementing the process of FIGS. 2A-2C that includes a logic device, such as a microprocessor or computer, or both, to receive sensor measurements, to execute a control algorithm or program to process the sensor measurements, and to generate instructions for the other system components. Although a blood saturation monitoring device, a cabin pressure altitude monitoring device or pressure sensor, an $O_2$ supply and a warning device must be on board the aircraft, a memory device as well as the logic device may or may not be on board the aircraft as will be discussed in additional detail below.

Referring back to FIG. 2A, initially, stored personalized data in step 20 such as physiological data taken at a particular cabin pressure altitude during previous flights, if available, is stored locally in a storage device for use by the logic device. The personalized data may be stored in the storage devices using different techniques and media as will be discussed in additional detail below. In step 27, which is preferably located before step 26, a cumulative clock time reference is initiated, from which all other recorded time references may be compared. The cumulative clock is controlled by the logic device, and may employ any conventional form of time measurement, such as day and chronological time measured from a time standard. The purpose of the cumulative time measurements is to permit, if desired, a convenient means to determine the time differential between any two data readings or even between first and/or second recorded time readings, since the first and second recorded time readings may be periodically reset. In step 26, a noninvasive monitoring device, such as a pulse oximeter, which is preferably attached to each passenger prior to the flight and a pressure sensor located in the aircraft cabin take respective readings at substantially the same instant of time. The pulse oximeter employs an LED and photosensor typically placed on opposite sides of an artery located in the passenger's tissue, although arteries close to the epidural surface may not require opposite side placement, possibly resembling a single flexible patch. The passenger tissue is transilluminated, the reduced amount of illumination that is sensed by the photosensor corresponding to a saturation level in the blood that is calculable by the logic device. The pressure sensor provides an output analog signal, typically a voltage, in response to the pressure level in the aircraft cabin. These readings are transmitted to the logic device in step 32 as either an analog or a digital signal, depending upon many factors, including the distance the signals must travel to reach the logic device. Both the body monitor reading and the pressure reading are separately compared to predetermined standards in a respective body monitoring branch beginning in step 41 (FIG. 2B) and a pressure monitoring branch beginning in step 62 (FIG. 2C).

Referring to FIG. 2B, in which the body monitoring branch begins at step 41, the body monitor reading taken in step 26 (FIG. 2A) is compared with a predetermined physiological standard associated with an increase risk of hypoxemia. In a preferred embodiment, the $SAO_2$ level of the subject matter is compared with a 91% standard. In step 53, if the body monitor reading meets this standard, the process checks for previous or sufficiently recent readings that had failed to meet the standard. If no previous readings failed to meet the standard, the body monitor/pressure data may optionally be transmitted to the data storage device in step 59 and then prepare to take the next body monitor/pressure reading in step 26. Conversely, if a sufficient number of previous readings in step 53 are received, in step 56 supplemental oxygen is then shut off from the passenger and first and fifth warnings are deactivated as will be discussed in additional detail below. However, if at step 41 the body monitor reading fails to meet the predetermined standard, possibly subject to a sufficient number of confirmation readings in step 44, a first warning message from a warning device is initiated in step 46 to alert the passenger and pilot. Preferably, the first warning message is in the form of an audio signal, although possibly combined with a visual signal for a viewing device that may be secured to the body monitor or to any portion of the exterior of the portable container for prominent and convenient viewing by the passenger. Supplemental oxygen is then provided to at least the passenger having the sub-standard body monitor reading in step 47, wherein the pilot may manually initiate supplemental oxygen to the particular passenger, or if the system is in electrical communication with the aircraft computer, in response to the receipt of the first warning signal, the aircraft computer may initiate supplemental oxygen. The current data readings, which contain both a signal corresponding to a cabin pressure altitude reading and a signal corresponding to a sub-par (below about 91% $SAO_2$) blood oxygen saturation level, may be transmitted to the memory device in step 50. These data readings represent a significant data reference for future flights for this particular passenger in that the cabin altitude pressure resulted in an increased risk of an onset of a hypoxemic condition for the passenger and will become part of that passenger's flight history which may be accessed from step 20 for comparison in step 62 of the pressure branch during future flights.

A further optional feature of the safety system includes a first predetermined time reference for providing enhanced passenger safety. Once supplemental on-board breathing oxygen is provided to the passenger in step 47, and the data is transmitted in step 50, a first recorded time reference is initiated in step 92 to monitor the approximate amount of time that supplemental oxygen in step 47 has been made available to the passenger. However, simply making supplemental oxygen available to the passenger does not ensure that the passenger has donned the oxygen mask to receive the supplemental oxygen. Thus, the purpose of the first recorded reference is to require the passenger to perform an affirmative act, such as actuating a switch, in addition to donning the oxygen mask. If the switch, which is preferably located on the monitoring device or on the container itself, is not reset, in step 93 the passenger may be impaired due to hypoxemia which could prevent the passenger from donning the oxygen mask for receiving the supplemental oxygen, placing the passenger at great risk. If the passenger has actuated the switch, the first recorded time reference is reset to zero in step 94. Otherwise the first recorded time reference continues to chronologically increment or increase in time duration. In step 95, the first recorded time reference is compared to a predetermined time increment. Although the first recorded time reference will not be exceeded initially in step 95, a fifth warning message may be initiated in step 96, preferably in an audio and visual format stating to the effect that the affirmative act must be taken, including donning the oxygen mask and actuating the desired switch to prevent further emergency actions from occurring. If the passenger permits the first recorded time reference to exceed the predetermined time increment, this may be indicative of hypersensitivity to the exposed cabin pressure level wherein the passenger is temporarily incapacitated. Since the passenger may be a pilot, possibly including a pilot flying solo, emergency procedures may be employed in step 98, including, but not being limited to, a decrease in aircraft altitude, necessitating a connection with the aircraft autopilot, broadcasting an automatic emergency message to a pre-programmed airport tower, accompanied by a second warning message broadcasting an audio message within the aircraft cabin using an elevated volume level to alert a possibly impaired pilot into responding to the emergency procedures. To accomplish altitude reduction, the autopilot and aircraft computer must be adapted to respond to signals received from the logic device.

Referring to FIG. 2C, the pressure monitoring branch begins in step 62, wherein the stored personal flight data provides the first measuring standard. In other words, for each passenger the stored altitude portion of this data corresponding to a sub-standard body monitor reading (at step 41, FIG. 2B) taken during a previous flight is employed as a comparator in step 62. For purposes herein, only stored altitudes corresponding to sub-standard body monitor readings in which the altitudes are less than the 12,500 feet MSL standard in step 74 are employed, because exposure to altitudes for predetermined time durations above this range are already being monitored by the process in compliance with FAA regulations as discussed below. If the current aircraft pressure altitude is greater than any of the stored "personal altitudes," a third warning message from the warning device is activated in step 71 to alert the passenger and pilot. However, no supplemental oxygen is dispensed unless the standard in step 41 is not met. Next, if the personal altitude in step 62 is greater than the cabin altitude, subject to possible conforming readings in step 65, in step 68 the third warning is deactivated if already activated, and the process returns to step 26 take an additional monitoring device reading. If the cabin pressure altitude in step 62 is exceeded, the aircraft altitude in the cabin is then compared to 12,500 feet MSL altitude in step 74. If the cabin pressure altitude exceeds 12,500 feet MSL, the aircraft altitude in the cabin is then compared to 14,000 feet MSL altitude in step 89. If the aircraft altitude is less than 14,000 feet MSL, a second recorded time reference is initiated in step 83 to correspond to the amount of time the aircraft is at an altitude that is equal to or greater than 12,500 feet MSL and less than 14,000 feet MSL. If the second recorded time reference meets or exceeds 30 minutes in step 86 or if 14,000 feet MSL is exceeded in step 89, a fourth warning message from the warning device is activated to alert the passengers in step 88 and supplemental oxygen from an on board source is made available for each passenger, such as by "drop down" face masks which each passenger typically secures over both his nose and mouth. Current FAA regulations only require providing supplemental oxygen to the minimum required flight crew at the 12,500-14,000 feet MSL range if the aircraft remains within that altitude range for 30 contiguous minutes. Upon achieving a cabin pressure altitude of at least 14,001 feet MSL in step 91, irrespective of time duration at that altitude, all passengers are provided with on board supplemental breathing oxygen for the entire duration of time in which the cabin pressure altitude is maintained at or above this cabin pressure altitude. The pressure branch does not include a comparison of cabin pressure altitude to 15,000 feet MSL for mandatory provision of supplemental oxygen to all passengers according to the FAA regulations. This is because the process of the present invention already provides supplemental oxygen to all passengers at a cabin pressure altitude exceeding 14,000 feet MSL. Comparative steps 74, 86 and 89 are configured to otherwise correspond with current FAA regulations in effect, at a minimum, with comparative step 41 establishing the minimum body monitoring readings for any cabin pressure altitudes less than those codified in the FAA regulations. For example, if the temperature outside the aircraft is 6° C. (42.8° F.) at a pressure altitude of 11,495 feet MSL, but the aircraft cabin temperature is at 27.3° C. (81.1° F.) at 20% humidity, the cabin density altitude is 15,325 feet. If desired, the safety system can be configured in pressure altitude, or any other calculated altitudes such as cabin density altitude, if desired, so in this instance, if cabin density altitude is used, supplemental oxygen would be dispensed since 15,325 feet exceeds the 14,000 feet threshold. In other words, the safety system of the present invention will always comply with the FAA cabin pressure altitudes, but is more stringent to help prevent harm to any passengers that may be unable to endure the minimum FAA pressure standards and to supply supplemental oxygen to all passengers, not just minimum required flight crew. Further, by utilizing personal flight data, those passengers that may be more susceptible to adverse effects from reduced cabin pressure altitudes will be identified to provide enhanced flight safety.

Referring back to FIGS. 2A-2C, all hardware associated with the safety system may be portable, with the possible exception of the monitoring device used in step 26. That is, the safety system which is otherwise incorporated within a single portable container may be brought on board the aircraft for use during the flight and removed from the aircraft upon completion of the flight and may be further dedicated for the use of a particular passenger. In other words, the safety system may be a stand-alone system for individual use. In step 20, stored personal data, if available, preferably contains a physiological reading, such as arterial blood oxygen content, $SAO_2$, as well as the preferred cabin altitude pressure, such as feet MSL, although other pressures such as cabin density pressure as previously discussed may be used, which personal data being taken substantially at the same time as the physiological reading so that the readings are sufficiently synchronized in chronological time. This stored personal data may reside on a portable memory device that is carried by the passenger and downloaded to the logic device, such as by inserting the portable memory device e.g., CD, diskette, DVD, flash memory card, etc., inside an appropriate reader connected to the logic device. In another embodiment the personal data may be resident in a memory device provided within the container. Preferably, the memory device has sufficient capacity to store multiple data readings at predetermined time intervals, predetermined altitude intervals, or both, as well as the capability to store such data at reduced time intervals if the blood saturation level begins to fall, especially as the blood saturation level approaches or falls below the standard in step 41. However, if the storage capacity of the resident memory device within the container is limited, the amount of data actually saved may be limited to those in which the blood saturation content is lowest for a particular flight, although preferably at least one data reading corresponding to significantly lowered blood saturation levels is also recorded. Additionally, multiple instances of significantly lowered blood saturation levels during a particular flight is preferably recorded. Optionally, in the case of multiple instances of significantly lowered blood saturation levels during a particular flight for a particular passenger may be recorded, subject to a sufficient recovery time. Recovery time is the duration of time passing between these instances of lowered blood saturation levels by comparing the cumulative clock reading when the first recorded time reference is reset, as well as the time duration that supplemental oxygen is supplied to the passenger. Any combination of this information may be provided in step 59 for possible storage in the storage device, if desired.

The stored personal data is used by the logic device housed within the container for periodic monitoring in step 62. Since the stored personal data preferably includes aircraft cabin pressure altitudes corresponding to blood saturation levels during previous flights, representing flight history information for the particular passenger, such information may be advantageously used to alert the passenger of cabin pressure altitudes associated with reduced blood saturation values. Therefore, if stored personal data for the particular passenger includes any significantly reduced blood saturation values at any cabin pressure altitudes less than those mandated by FAA regulations for providing or conditionally providing passengers with supplemental oxygen (currently 12,500 and 14,000 feet MSL in respective steps 74 and 89), the lowest of those cabin pressure altitudes may be provided as an altitude standard for comparison in step 62. That is, the lowest cabin pressure altitude that has previously corresponded to the passenger's reduced blood saturation value may be used as a baseline comparison with the cabin pressure altitude in the current flight. If the cabin pressure altitude of the current flight is equal to or exceeds the stored data altitude level, a third warning message from a warning device secured within the portable container, such as an audio message possibly accompanied by a visual display on the monitoring device, is initiated in step 71 as previously discussed and may be repeated at predetermined time or increased altitude increments. This personalized stored data typically correlates to future reduced blood saturation values for the same individual, and although subject to gradual change over time, is a valuable precautionary criterion for establishing heightened awareness of hypoxemic conditions and preventing potential catastrophic results.

Even if step 62 of the pressure branch of the safety system provides the passenger with the third audible warning message, so long as the passenger's current blood level remains at or above the standard in step 41 of the body monitoring branch, the aircraft may continue with its flight plan, which may include achieving greater cabin pressure altitudes. Alternatively, if a particular passenger's current blood level fails to meet the standard in step 41, supplemental oxygen may be provided to that passenger only to efficiently utilize the limited supply of supplemental oxygen. Upon the passenger having a sufficient number of consecutive compliant blood saturation readings in step 53, the supplemental oxygen is shut off to the passenger in step 56 wherein the passengers resume inspiring the unpressurized cabin air.

In another embodiment of the processes of FIGS. 2A-2C-4A-4C, instead of comparing the altitude standard in feet MSL, as currently identified in the FAA regulations, the cabin density altitude can be compared by utilizing a temperature sensor incorporated within the portable container which operates similarly to the pressure sensor in step 26. The temperature sensor provides an output signal, such as a voltage, in response to a temperature level within the cabin. The temperature and pressure signals are transmitted from the pressure sensor and temperature sensor to the logic device, and the cabin density altitude is then calculated by the logic device utilizing the previously discussed formulas.

Figure 3A:
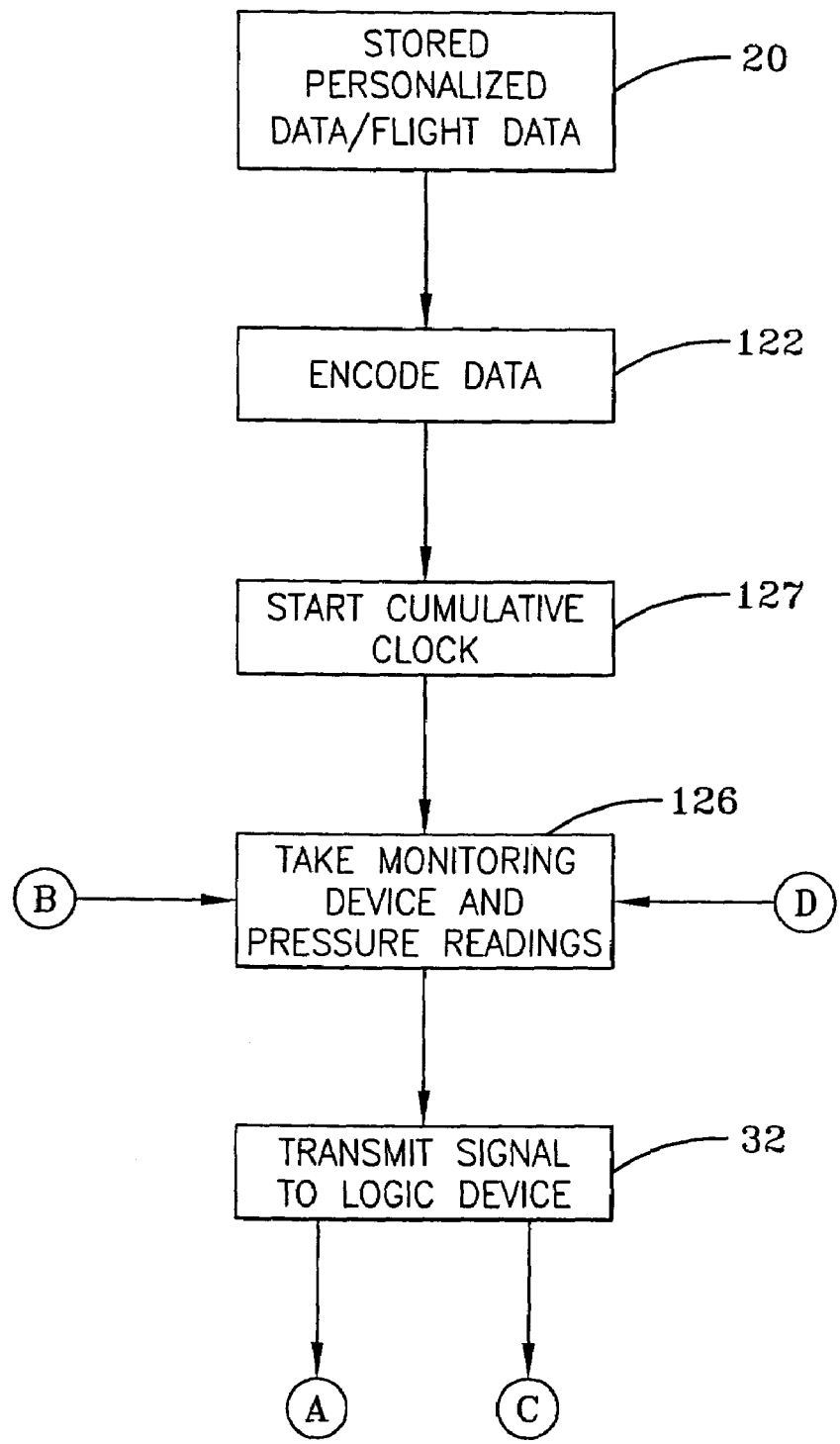
FIGS. 3A-3C and 4A-4C are process diagrams corresponding with the operation of alternate embodiments of the system of the present invention.
Figure 3B:
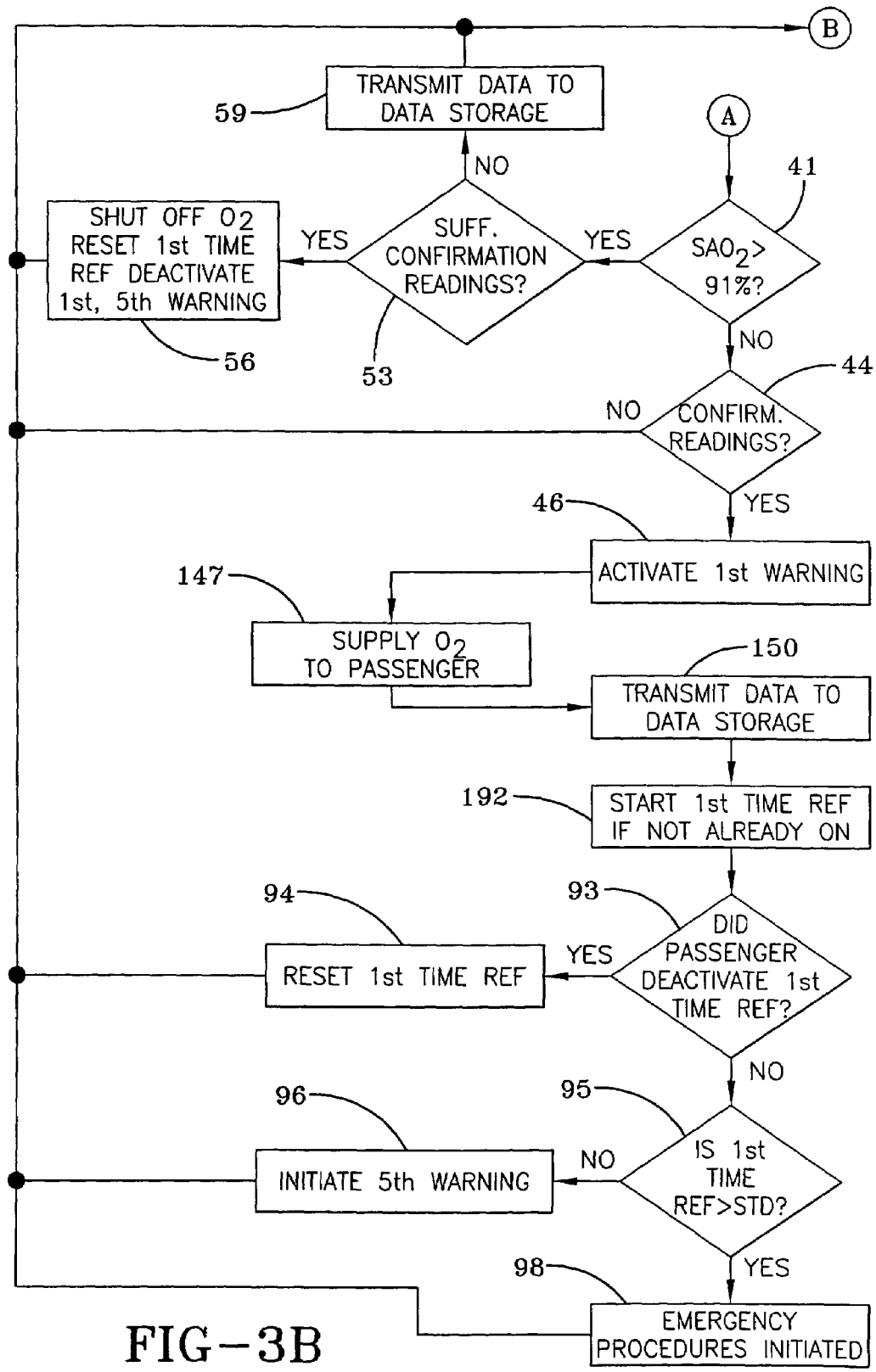
Figure 3C:
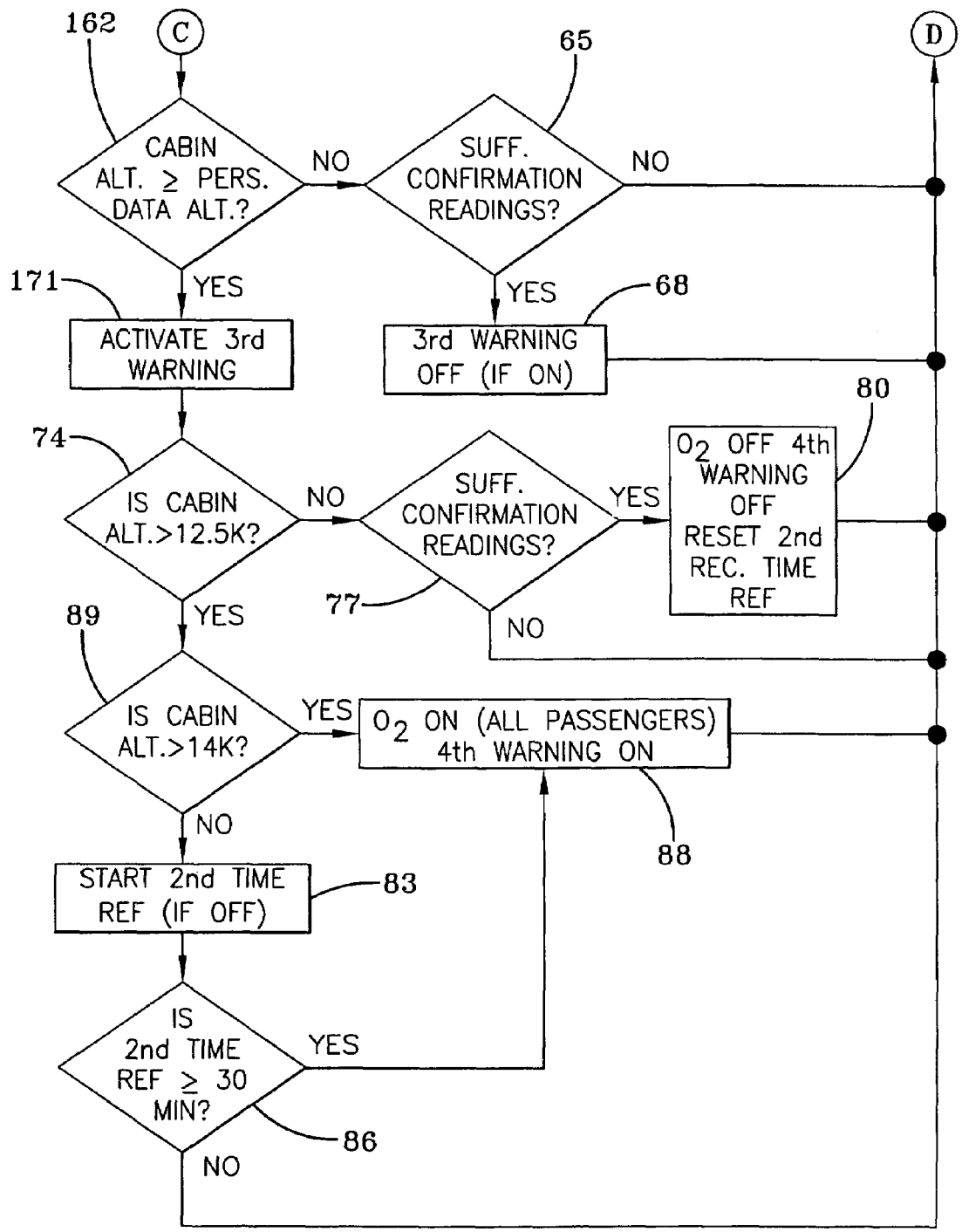

Referring now to FIGS. 3A-3C, which are the same as FIGS. 2A-2C unless otherwise indicated and collectively illustrate an embodiment of the safety system for use with more than one person. That is, any number of passengers in the aircraft may be simultaneously monitored with the safety system in FIGS. 3A-3C. Therefore, the primary differences between FIGS. 2A-2C and 3A-3C are reflected in the need to continually maintain the correlation between each passenger and his data, whether stored personal data from previous flights or physiological/pressure readings. For example, in step 122, which is inserted after step 27 in FIG. 3A, the stored personal data is preferably converted to encoded data to differentiate the data for each passenger. This may be accomplished by differentially grouping the data of each passenger, providing different frequencies for each passenger when transmitting the data, or by other data transfer techniques known in the art. Alternately, while it may also be possible to maintain multiple hardware connections to unique ports between each of the hardware components located adjacent each other so that signal differentiation by encoding may not be required, FIGS. 3A-3C and 4A-4C will reflect the differentially encoded construction. Thus, steps 150 and 159 are substantially similar to respective steps 50 and 59 except for the additional clarification that the particular signal is encoded. Similarly, step 126, otherwise similar to step 26, further clarifies that monitor and pressure readings may be taken for each passenger. Alternately, in step 126 if monitor readings can be taken sufficiently quickly, usually up to a few seconds, a single pressure reading may be taken and combined with each of the monitor readings for each passenger since the pressure reading would likely have changed very little within that short period of time. Steps 147, 192 and 195, otherwise similar to steps 47, 92 and 95, each further clarifies that the respective step refers to the particular passenger whose data is being analyzed. In other words, supplemental oxygen is supplied to the particular passenger (the "correct passenger") whose blood oxygen level was confirmed as being sub-par in step 44 (FIG. 3B). The majority of the steps associated with the pressure branch, that is, starting with step 162 (FIG. 3C) and returning to step 126 (FIG. 3A) are unaffected. That is, with the exception of steps 162 and 171 previously discussed which each include personalized stored data and require encoding to correspond to a particular pressure, the altitude standards, which are fixed by FAA regulations, do not change. Similarly, no signal encoding is required since any provided supplemental oxygen is supplied to all passengers.

Further referring to the process in FIGS. 3A-3C, all the hardware is included within the aircraft, preferably permanently secured therein. Step 20 is differentiated by the source of stored personal data which resides in a memory device contained within the aircraft, possibly within a portion of the memory device in the aircraft computer system. The container previously discussed in FIGS. 2A-2C which houses all the sensing components may still be utilized, except it is also preferably secured permanently within the aircraft, more preferably incorporated into the structure of the aircraft for aesthetic reasons. Alternately, the logic device may be coupled with or incorporated into the aircraft computer, making it possible, if preferred, to totally incorporate all data control of the safety system within the aircraft computer, further possibly including all temperature and pressure sensors which are positioned to take readings that accurately reflect cabin pressures and temperatures.

Figure 4A:
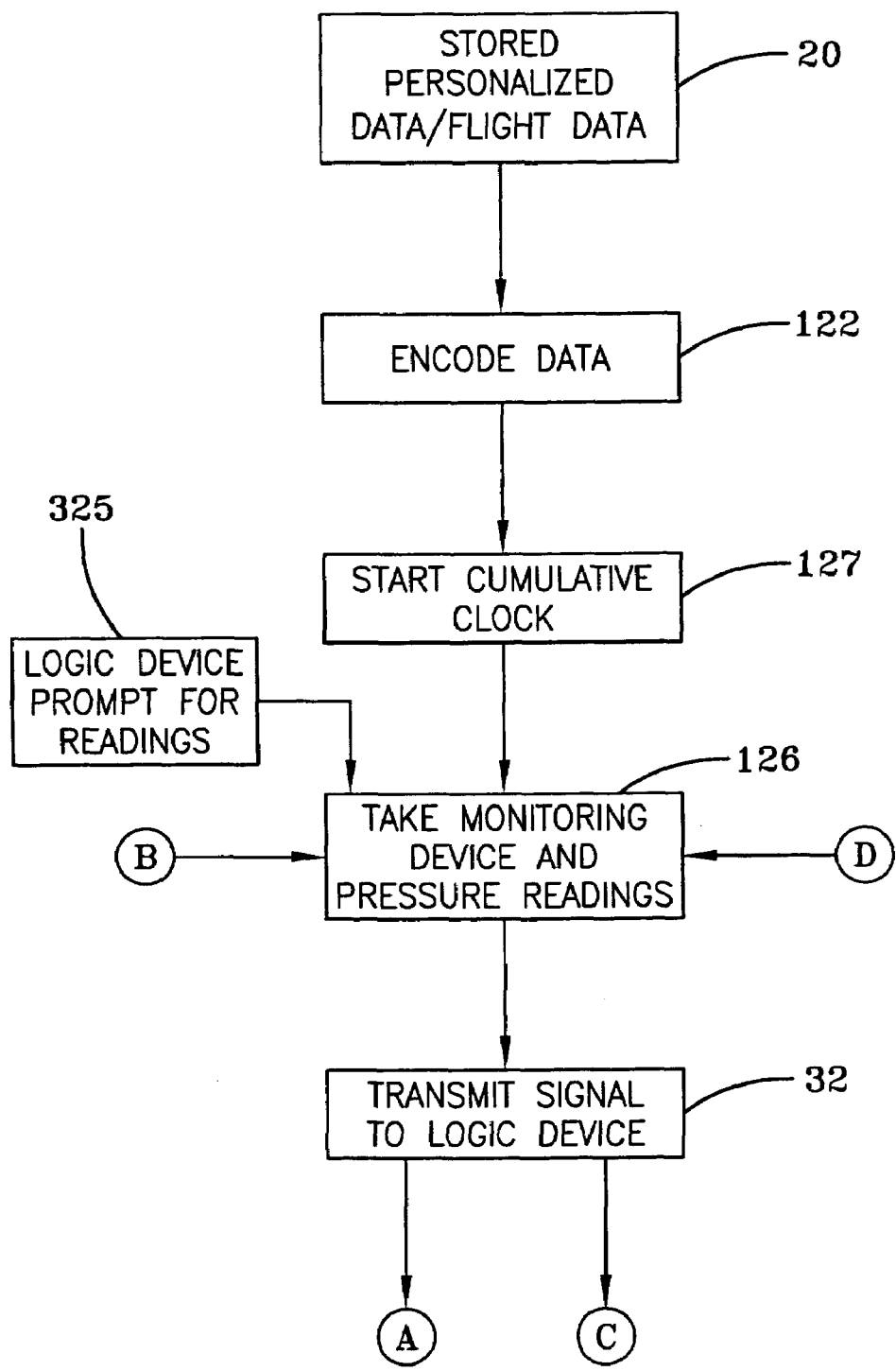
Figure 4B:
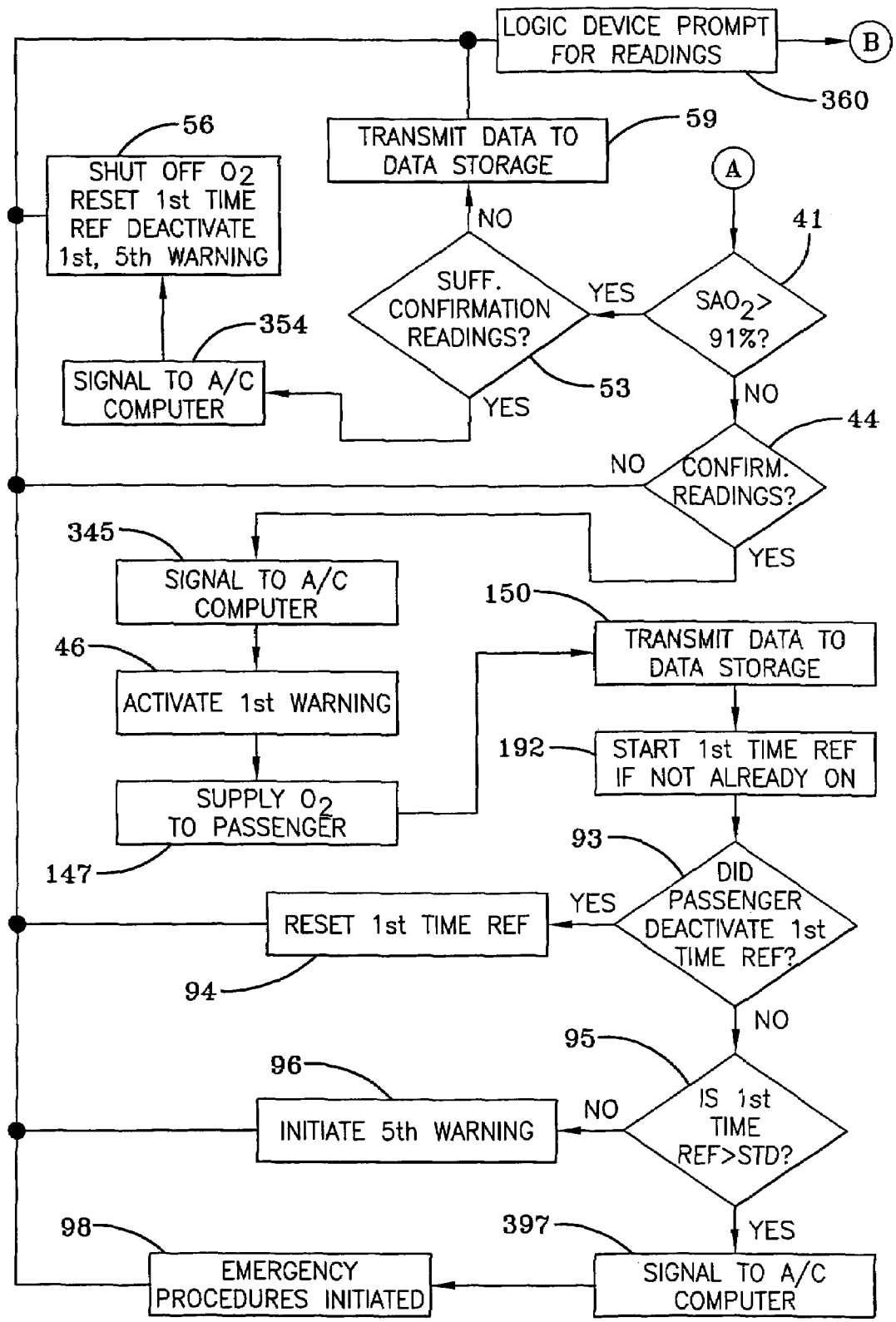
Figure 4C:
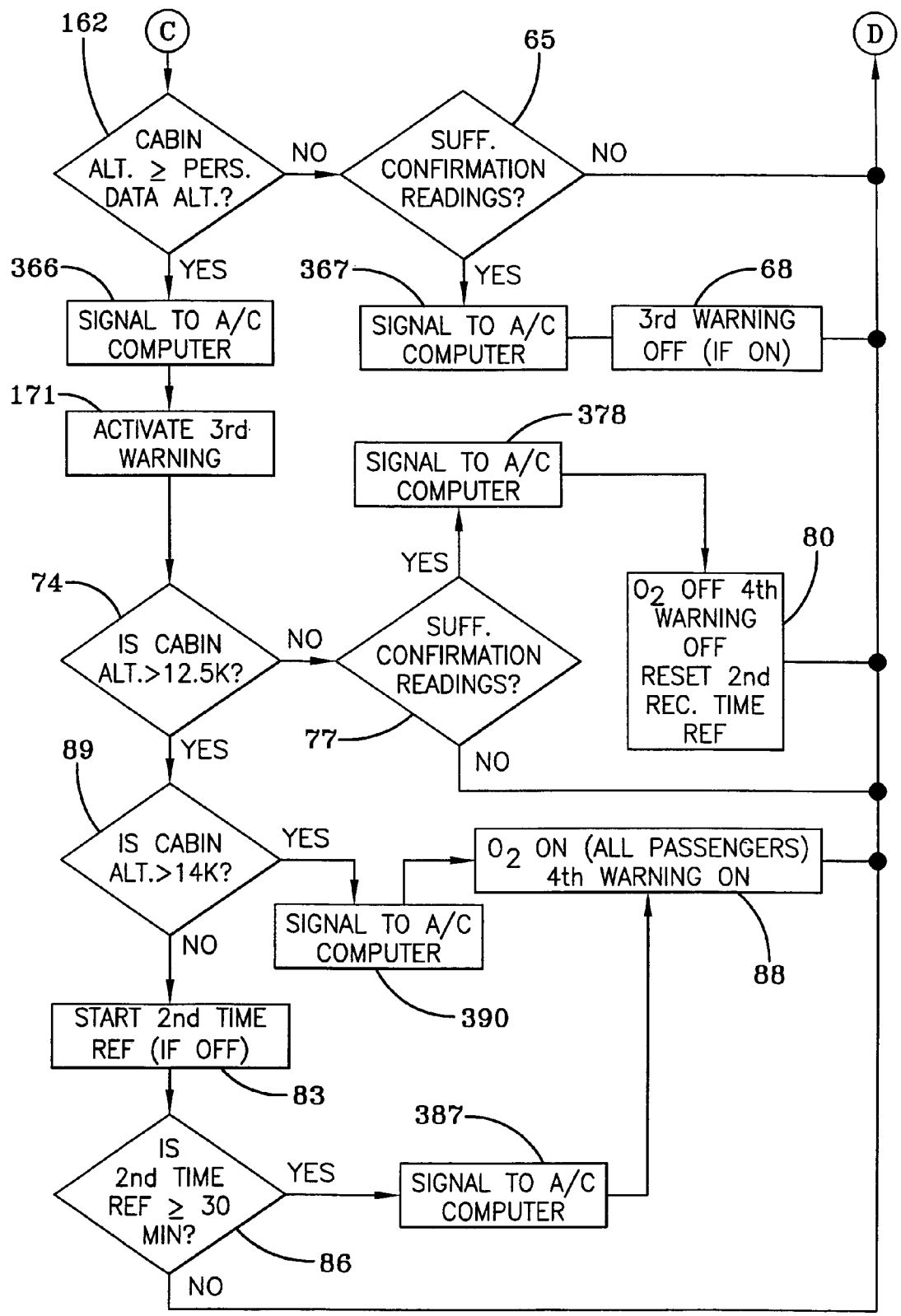
Figure 5:
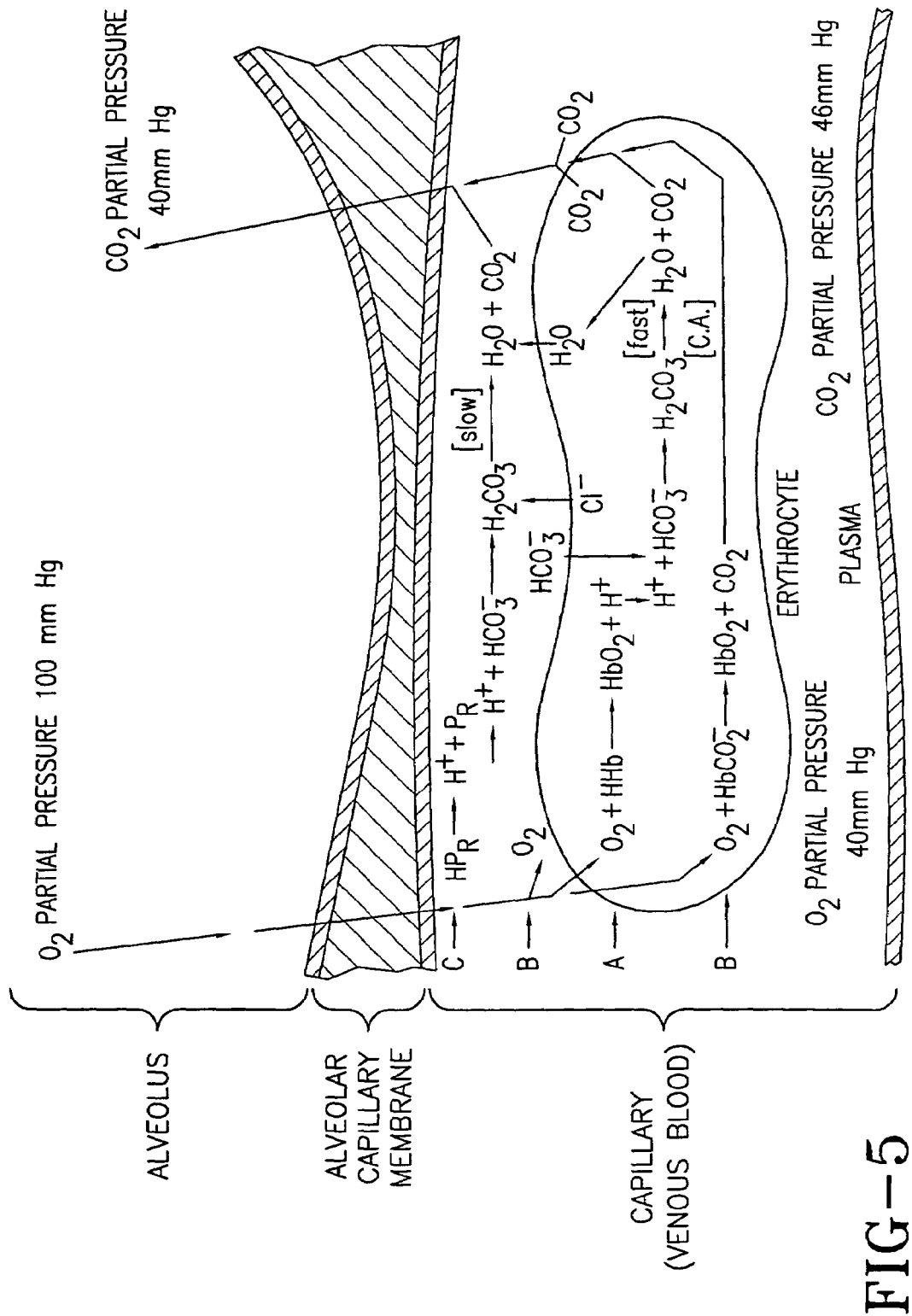
FIG. 5 is a diagram illustrating blood gas chemistry between a capillary and an alveolus.

Referring to FIGS. 4A-4C, a further embodiment of the safety system includes remotely locating a number of the safety system components from the aircraft. It is possible for all components except for on board sensors, including the body monitor, pressure and temperature sensors, and warning device to be remotely located, so long as there is a receiving/sending device(s) capable of responding to request signals from a remotely located logic device. In step 20 (FIG. 4A), all stored personal flight data, including at least blood saturation levels at corresponding cabin pressure levels, may be secured in a memory device remotely located from the aircraft, preferably for common data storage/retrieval by all aircraft having unpressurized cabins. To access this personal flight data, following encoding and digitizing the respective signals as previously described in steps 21 and 122, the signal is preferably amplified and transmitted to a logic device at step 23 for comparison with the current cabin altitude pressure of the aircraft during flight. The logic device is also possibly remote from both the data storage location and the aircraft. The cabin altitude pressure comparison required at step 162 is provided by a prompting signal from the logic device in step 325 which is received by a receiving device in the aircraft that causes the synchronized body monitor and cabin pressure altitude readings in step 126 to be taken. The readings taken in step 126 are preferably amplified by a amplifier and converted to a digital signal before being transmitted. In step 32, the resulting signal may now be transmitted, such as by the aircraft radio transmitter to a receiving device in data communication with the remote logic device. Upon receipt of the digitized pressure/blood saturation data, the most current altitude information from the aircraft may be determined as well as the blood saturation level for a particular passenger in the aircraft. In step 162 (FIG. 4C), the calculated aircraft altitude is compared to the established standard(s), which preferably correspond to the minimum aircraft altitudes of stored personal data obtained in step 20 for each of the passengers. If the current aircraft altitude is greater than this standard for any of the passengers, the logic device transmits a radio signal that is received by a receiving device in the aircraft in step 366 directing that the third warning message from the warning device in step 171 be activated. This third warning message serves to alert at least the one passenger and the pilot, assuming they are not the same person, that the aircraft is at or above an altitude that had previously corresponded to a sub-par blood saturation level reading for a particular passenger during a previous flight. Thus, it may be possible that multiple third warning messages may be issued, one for each passenger likewise having stored personal data in which the aircraft altitude corresponds to a sub-par blood oxygen saturation level reading. While the same passenger may have over time several stored data readings in which multiple aircraft altitudes have corresponded to sub-par blood oxygen saturation levels, only the lowest such altitude need be used as a comparative standard for each passenger in step 162.

The same most recently obtained altitude information utilized in step 162 is now compared to a first predetermined FAA altitude standard in step 74 as previously discussed. If the first predetermined altitude is exceeded, in step 89 the altitude information is then compared to a second predetermined FAA altitude standard as previously discussed. If the second predetermined altitude is not exceeded, a second recorded time reference is initiated, preferably remotely in the logic device, in step 83 as previously discussed. If the second recorded time reference, representing a predetermined FAA contiguous time duration that the aircraft altitude is between the predetermined altitude standards in step 74 and step 89, exceeds 30 minutes by current FAA regulations in step 86, the logic device transmits another radio signal that is received by the receiving device in the aircraft in step 387 directing that the fourth warning message from the warning device in step 88 be activated to so warn all the passengers, and further that supplemental on board oxygen source be provided to all passengers as previously discussed. Optionally, the signal in step 387 could activate a solenoid valve member in fluid communication with the supplemental on board oxygen source so that upon receipt of the signal by the receiving device, the solenoid is placed in an open position, providing supplemental breathing oxygen to all the passengers.

In case the most recently obtained altitude information exceeds the second predetermined FAA altitude in step 89, which requires the immediate provision of supplemental breathing oxygen as previously discussed, the logic device transmits a radio signal that is received by the receiving device in the aircraft in step 390 directing that the fourth warning message from the warning device in step 91 be activated to so warn all the passengers, and further that supplemental on board oxygen source be provided to all passengers. Optionally, the signal in step 390 could activate a solenoid valve member in fluid communication with the supplemental on board oxygen source so that upon receipt of the signal by the receiving device, the solenoid is placed in an open position, providing supplemental breathing oxygen to all the passengers.

If the aircraft descends until the cabin pressure altitude based upon the latest readings taken in step 126 (FIG. 4A) is less than the FAA predetermined altitude in step 74 (FIG. 4C), subject to confirmation step 77 possibly requiring additional compliant readings or contiguously compliant readings for a sufficient time duration, the logic device resets the second time reading then transmits a radio signal that is received by the receiving device in the aircraft in step 378 directing that the fourth warning message from the warning device in step 91 be deactivated and further that the supplemental on board oxygen source is no longer required, according to FAA regulations. Optionally, the signal in step 378 could activate a solenoid valve member in fluid communication with the supplemental on board oxygen source so that upon receipt of the signal by the receiving device, the solenoid is placed in a closed position.

If the aircraft further descends until the cabin pressure altitude based upon the latest readings taken in step 126 (FIG. 4A) is less than the stored person data altitude values for all passengers, obtained from step 20, in step 162 (FIG. 4C), subject to confirmation step 65 possibly requiring additional compliant readings or contiguously compliant readings for a sufficient time duration, the logic device transmits a radio signal that is received by the receiving device in the aircraft in step 367 directing that the third warning message from the warning device in step 68 be deactivated.

Returning now to the body monitoring branch which begins at step 41 (FIG. 4B), the most recent blood oxygen saturation level for a particular passenger is compared with a predetermined clinical oxygen saturation level standard as previously discussed. If the most recent blood saturation level fails to meet the predetermined level in step 41, possibly subject to a confirmation step 44 which may further require a sufficient number of consecutive sub-par blood saturation level readings to further reduce the possibility of a false positive reading, the logic device transmits a radio signal that is received by the receiving device in the aircraft in step 345 directing that the first warning message from the warning device in step 46 be activated to so warn the passenger, and further that supplemental on-board oxygen source be provided to the passenger. Optionally, the signal in step 345 could activate a solenoid valve member in fluid communication with the supplemental on-board oxygen source so that upon receipt of the signal by the receiving device, the solenoid may be placed in an open position to provide the passenger having the sub-par blood oxygen level with supplemental breathing oxygen from the supplemental oxygen source in step 147. Once the provision of supplemental breathing oxygen to the passenger has begun, the encoded passenger data signal originally read in step 126 (FIG. 4A) may then be transmitted to the remote memory device in step 150. Upon receipt of the passenger data in step 150 by the logic device, the logic device then transmits a prompting signal to the receiving device in the aircraft in step 360 to take another set of readings in step 126 for a particular passenger. Preferably, the query sequence performed by the logic device in step 360 systematically increments between passengers at predetermined time increments or at aircraft altitudes compared against those altitude levels calculated for initial comparison with predetermined altitude standards in step 162 (FIG. 4C).

Alternately, if the most recent blood saturation level meets the predetermined level in step 41, possibly subject to a confirmation step 53 which may further require a sufficient number of consecutive compliant blood saturation level readings to further reduce the possibility of a false negative reading, the logic device transmits a radio signal that is received by the receiving device in the aircraft in step 354 directing that the first warning message from the warning device in step 56 be re-set, and further that the supplemental on board oxygen source be shut off. Optionally, the signal in step 354 could activate a solenoid valve member in fluid communication with the supplemental on board oxygen source so that upon receipt of the signal by the receiving device, the solenoid may be placed in a closed position to conserve the supplemental oxygen source for possible further use.

Referring to the optional sequence starting at step 192 (FIG. 4B) that is positioned near the end of the body monitoring branch as previously discussed, in response to the first recorded time reference being initiated in step 192, and further upon the first recorded time reference exceeding the predetermined time standard in step 195, possible emergency procedures may be initiated in step 98. To initiate step 98 in FIG. 4B, the logic device transmits another radio signal that is received by the receiving device in the aircraft in step 397. Preferably this radio signal is associated with control over the aircraft computer, more specifically the aircraft autopilot, such that the aircraft altitude may be reduced to a predetermined level. The step 397 signal may additionally direct a second warning audio message be repeatedly broadcast by the aircraft warning device within the aircraft cabin using an elevated volume level to alert a possibly impaired pilot into responding to the emergency procedures. Similarly, the signal in step 397 may also activate the warning device to broadcast an automatic emergency message to a pre-programmed airport tower to alert of possible altitude related pilot impairment.

Optionally, the safety system of the present invention may calculate cabin density pressure altitude instead of MSL altitude for reasons previously discussed. In other words, while following the absolute values of the cabin altitude pressures as cited in the controlling FAA specifications, cabin density altitude would be calculated and applied throughout for all altitude values instead of MSL altitude. Cabin density altitude should always be greater than MSL altitude at the altitudes of interest, above 5,000 feet, since the cabin temperature should always exceed the temperature of the air surrounding the airplane at altitude. However, these altitudes may be compared, and the lower of the two selected for use with the safety system. Thus, the selected altitude will always fall within FAA regulations referring to MSL altitude. This will greatly enhance the safety for those traveling in unpressurized aircraft cabins.

Alternately, personal data in step 20 may be expanded to include, in a succinct fashion, at least some conditions that may cause the subject to be more susceptible to adverse effects from altitude. These conditions may include recent exertion level, hydration, in addition to the anticipated flight plan parameters, including rate of ascent, as well as the greatest anticipated flight altitude and anticipated duration at that highest or near highest altitude levels. This information could be manually input by a keypad in data communication with the memory device. As more is learned about the relationships between such physiological factors, these factors may be used to predict passenger susceptibility to altitude.

The monitoring device in step 26 is preferably a pulse oximeter which monitors arterial red cell oxygen saturation levels as previously discussed. Alternately, or at least in addition to the pulse oximeter, other monitoring devices may be employed that may be utilized to monitor any number of other physiological aspects such as inspiration/expiration analyses, so that oxygen saturation levels, or even some other single physiological measurement or combination of measurements may be calculated or obtained that may also be indicative of an increased risk of hypoxemia. Accordingly, while the comparison between a subject's oxygen saturation level and predetermined clinically accepted level of about 91% oxygen saturation in step 41 is preferred, an alternate testing criteria for a similarly accepted clinical indicator of an increased risk of hypoxemia may also be used. Therefore, some if not all of the comparative or confirmation steps as well as supplemental oxygen supply/shutoff steps may or may not be similar, or even appropriate, depending upon the nature of the type of physiological measurement taken.

Figure 7:
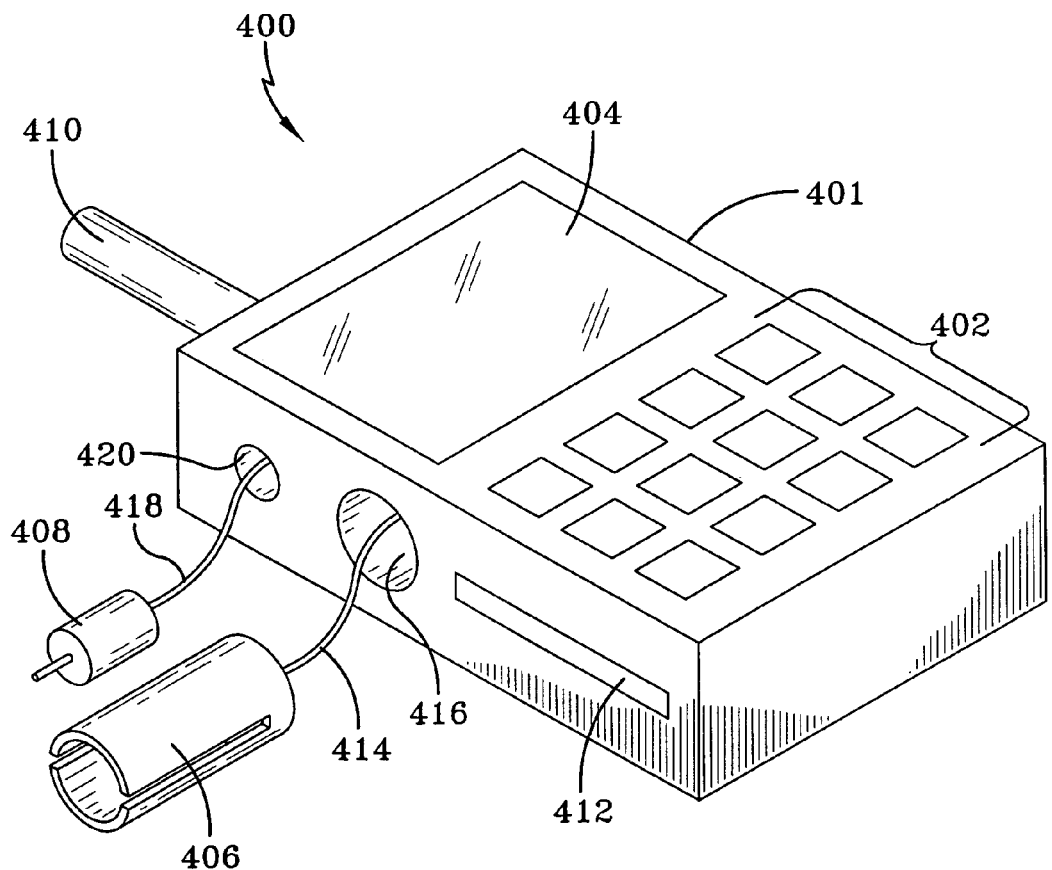
FIG. 7 is a perspective view of a devise usable to plan oxygen usage for an aircraft flight.
Figure 8:
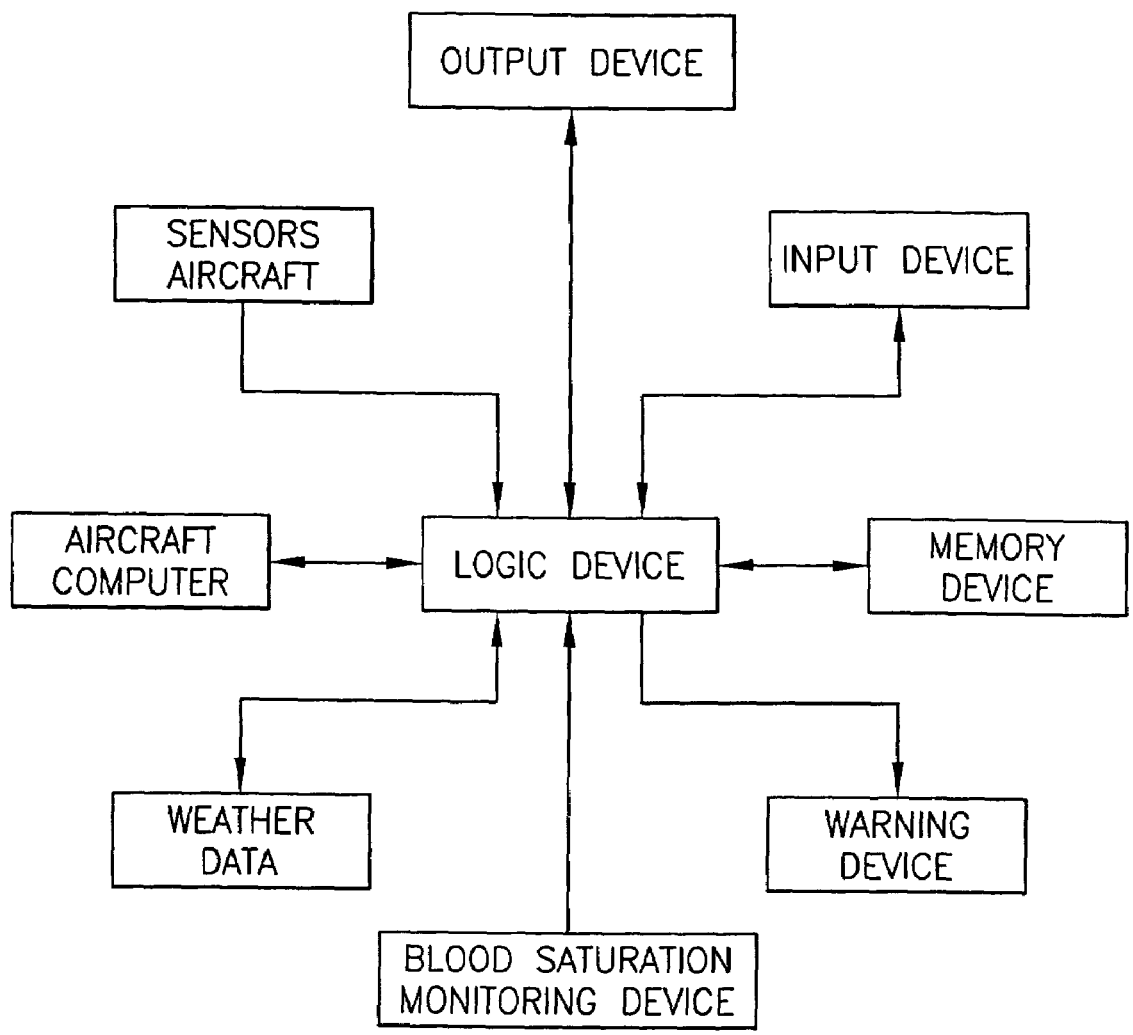
FIG. 8 is a general schematic illustrating the components of the device of the present invention.

Referring to FIGS. 7 and 8, a device 400 is configured for estimating oxygen usage for aircraft operating with unpressurized cabins, especially heated, unpressurized cabins, based on cabin pressure altitude, or alternately, other altitude measurements, such as cabin density altitude, as previously discussed. Device 400 includes a compact body 401 for securing therein an input device 402, such as a key pad, and an output device 404, such as a display monitor. Body 401 may of similar size with a handheld EB-6 military flight calculator, and preferably, the features of the EB-6 calculator are combined with the features of device 400 including arithmetic functions, unit of measure conversions, time keeping and time zone calculation and conversion functions, as well as multiple aviation functions. For convenience, the output device 404 may be a touch sensitive display screen, permitting a user to select displayed information such as flight parameters without having to interact with the input device 402. A logic device, not shown, controls the input and output devices 402, 404, a storage device, not shown, and performs flight parameter calculations. The input device 402 may be employed by the user to select and provide values for desired flight parameters, passenger information, oxygen storage information on board the airplane, or to select a desired flight parameter that the user wishes the device to calculate, depending on the mode of operation of the device which will be discussed in additional detail below. In addition, the device prompts the user for flight leg information, and calculates estimated oxygen requirements for the flight, as will be discussed in further detail below. The device 400 in its most basic form includes the input and output device 402, 404, logic device and storage device. Thus, in its most basic form, the user must input all known flight parameters into the device.

However, device 400 may optionally include multiple enhancements to either supplement or even automate the collection and calculation of the flight parameters required for oxygen flight planning, additionally providing, if desired, updated flight parameter information of an on-going flight. Optionally, a blood oxygen monitoring device clip 406 is provided with the device 400, functioning as previously discussed. The clip 406 extends from the body 401 by a wire 414 that is in data communication with the logic device as previously discussed, the clip 406 being insertable inside aperture 416 formed in body 401 when the clip 406 is not in use by the user. Alternately, the clip 406 may be molded into body 401, or even integrally incorporated inside the body 401 wherein the user may insert a finger inside aperture 416 to obtain a blood oxygen reading. Optionally, an adapter 408, or communication connection, interfaces with the aircraft computer or on-board sensors to provide flight parameters and/or specific oxygen storage information unique to the particular aircraft to the logic device. The adapter 408 extends from body 401 by a wire 418 which is similarly in data communication with the logic device as previously discussed between clip 406 and the logic device. The adapter 408 is also insertable into aperture 420 formed in body 401 when not in use. Alternately, if device 400 incorporates wireless technology, the adapter 408 may not be required, the device 400 employing such internal components to effect similar communications with the aircraft computer to provide the same information as could be obtained by the use of adapter 408. Further, an antenna 410 extends from body 401 to obtain flight parameters from sources other than the aircraft, such as weather stations, or other remote location as previously discussed, if desired. Alternately, antenna 410 may be incorporated within body 401 if the antenna 410 provides sufficient range for obtaining the desired flight parameter information. Optionally, an interface 412 is provided for transferring digital information to the logic device from an exterior storage medium, such as a floppy disk or compact disk in body 401. Alternately, the interface 412 may be a port configured for connecting with a corresponding data port fitting for transferring digital information from the storage medium to the logic device. Upon connection of the exterior storage medium with the interface 412, information may be transmitted to the logic device from the exterior storage medium or information from the device may be saved to the exterior storage medium. Such information may include personal flight information such as cabin pressure altitude or cabin density altitudes or $PO_2$ levels, including any of ambient, tracheal or alveolar as appropriate, corresponding to $SAO_2$ levels less than 91% as previously discussed for each of the passengers on the airplane.

Another embodiment of device 400 has self-contained sensors including a pressure sensing device, such as an aneroid barometer, and a temperature sensing device, thereby permitting calculation of cabin pressure or cabin density altitudes without the need for communicating with external sources. Alternately, the device 400 could incorporate sensors configured to analyze a user's respiratory parameters, obtainable by analyzing a user's inhalation and/or exhalation, including but not limited to peak expiratory flow rate (l/min), forced vital capacity (l/min), forced expiratory volume (l), expired $CO_2$ content (%), respiration rate (respirations/min) and any ratios of these parameters to obtain the user's $PCO_2$ levels, or other related information. Additionally, cardiovascular parameters including but not limited to heart rate (beats/min), mean arterial blood pressure (mmHg), cardiac index (l/min/m$^2$), left ventricular stroke index (ml/m$^2$), systemic vascular resistance index (dyn/sec/cm$^5$/m$^2$), thoracic fluid content (kohm$^{-1}$) or any other parameters employing impedance cardiology, also referred to as thoracic electrical bioimpedance, or any ratios of these parameters or combined with any other parameters may be utilized. Further, any of these parameters may be compared with the time to desaturate (sec) below an $SO_2$ level of 91 percent as a function of rate of ascent (feet/min).

A further embodiment of device 400 is a personal digital assistant, commonly referred to as a PDA, wherein the capabilities of device 400 are incorporated preferably by a software/hardware upgrade to the PDA, also referred to as an "add-on" such as a "memory stick" which is inserted into a port in the PDA. Alternately, the software upgrade may be achieved by remote download wherein the PDA is placed in data communication with the software download source having a storage medium such as a compact disk, or on-line data communication from the internet as is commonly known in the art.

Figure 9:
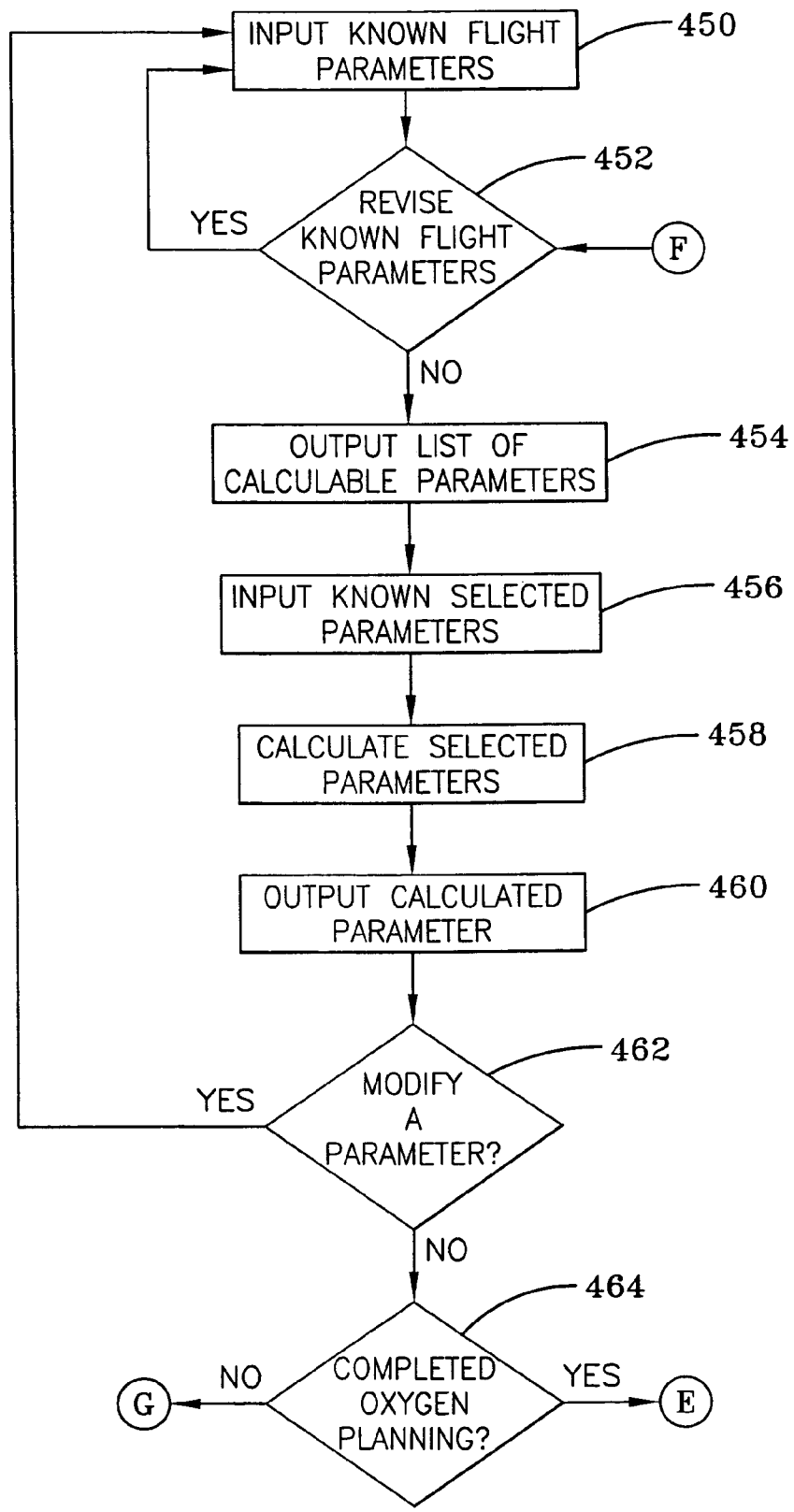
FIG. 9 is a diagram of a first operating mode of the device of the present invention.
Figure 9A:
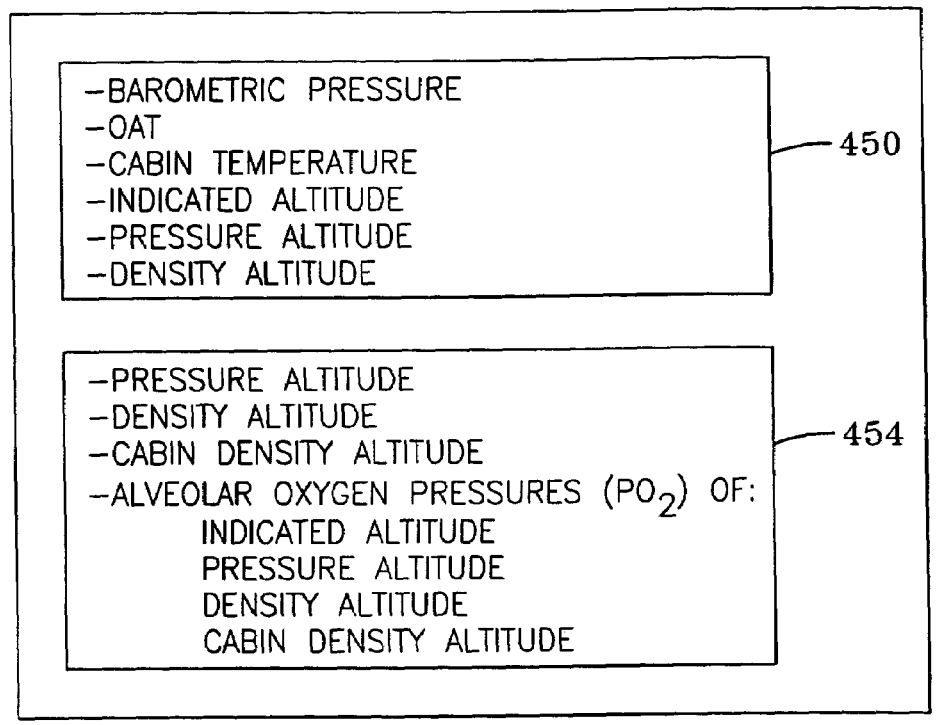
FIG. 9A is a detailed portion of the first operating mode of the device of the present invention illustrating representative known and calculable flight parameters.

The present invention further includes a first operating mode for device 400, referring to FIGS. 9 and 9A, for inputting and calculating flight parameters used for estimating oxygen requirements for an aircraft flight. A second operating mode will be discussed in additional detail below. Upon completion of the first operating mode, FIG. 9, the user is directed to the oxygen planning procedure, FIGS. 13A-13B, if the user has not yet completed the oxygen planning procedure. The oxygen planning procedure prompts the user to input the number of passengers as well as personal flight data for each passenger, if available. If personal flight data is unavailable for any passenger, the user may then input estimated flight data values or specify that the device provide estimated values. But if the user has previously completed the oxygen planning procedure, the user is then directed to FIG. 13B which is the modification portion of the oxygen planning procedure wherein the user may modify any previously selected values for any parameters in the oxygen planning procedure, followed by calculating and outputting the oxygen requirements for each leg of the flight. If desired, the user may return to the first operating mode, FIG. 9, to again modify any previously provided flight parameter, followed by returning the user to the modification portion of the oxygen planning procedure, FIG. 13B.

The first operating mode of device 400 prompts the user to input any known parameters in step 450. Such parameters may include, but are not limited to, the barometric pressure, OAT, and cabin temperature. Upon the user entering all known parameters in step 452, the user is prompted to correct any of the parameters that may have been incorrectly input in step 450. After the user has indicated that all known flight parameters are correct, device 400 then provides a list of all the parameters on the display device 404 that may be calculated from the flight parameters that had been input in step 450. Referring to FIG. 9A, if the following flight parameters in step 450 are provided, including the barometric pressure, OAT, cabin temperature, as well as the indicated altitude, the pressure altitude and the density altitude, it is then possible for the logic device in device 400 to calculate the values of the following parameters which would then be identified on the display device 404 in step 454: pressure altitude, density altitude, cabin density altitude, ambient, tracheal and/or alveolar oxygen pressure ($PO_2$) of indicated altitude, pressure altitude, density altitude and cabin density altitude. One skilled in the art can readily appreciate that due to the interrelationships between these parameters as identified in the previously provided equations, it is impractical to attempt to provide a comprehensive list of all the possible combinations of flight parameters that could be included in steps 450 and 454. However, it is believed that the most prominent and important parameters have been provided herein. The present invention may be configured to incorporate and/or calculate additional respiratory, cardiovascular, hydration or other physiologic parameters or ratios therebetween as previously discussed that may be shown to relate to $SAO_2$ levels.

Once all the calculable flight parameters have been identified in step 454, the user then selects all the desired parameters for device 400 to calculate in step 456. Upon the user making the selections of the desired parameters in step 456, those selected parameters are calculated by the logic device in step 458 and output for viewing on output device 404 in step 460. Once step 460 has been completed, the user is again prompted in step 462 as to whether any of the previously provided parameters in step 450 should be modified. If the user indicates that a parameter should be modified in step 462, the operating mode returns to step 450 and the user is given the opportunity to then modify any parameters as previously discussed. However, if the user does not wish to modify any parameters in step 462, upon so indicating on either the input device 402 or output device 404 as previously discussed, in step 464 the user is directed to the oxygen planning procedure (FIGS. 13A-13B) if the user has not previously been directed to the oxygen planning procedure. However, if the user has previously been directed to the oxygen planning procedure, the user is directed to the modification portion (FIG. 13C) of the oxygen planning procedure.

Figure 13A:
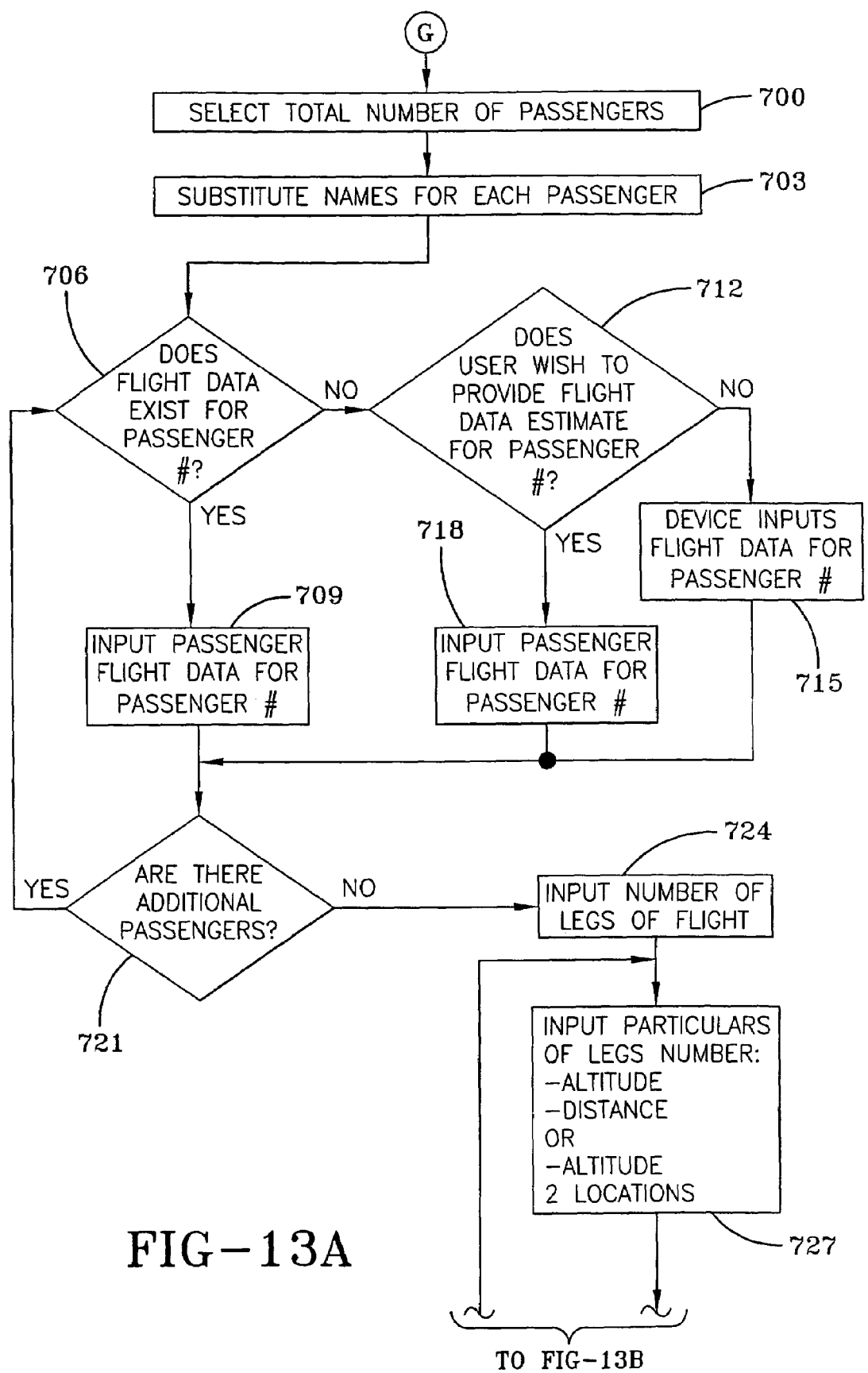
FIGS. 13A-13B is a diagram of an oxygen planning procedure of the device of the present invention.
Figure 13B:
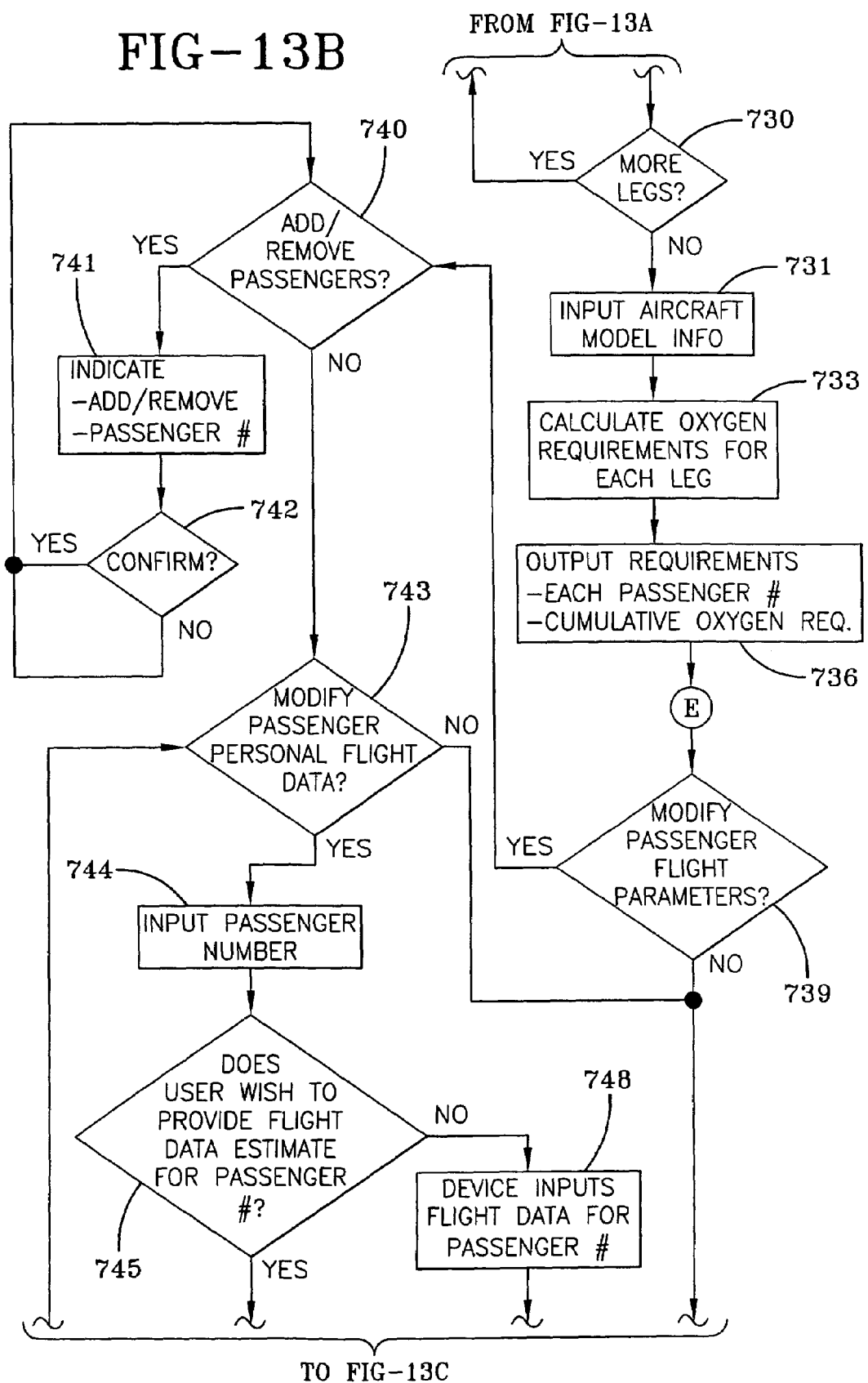

If the user is directed to the oxygen planning procedure, referring to FIGS. 13A-13B, in step 700 the user is prompted to input the total number of passengers on the flight, including the pilot. Optionally, for ease of identification between different passengers, in step 703 the user may, if desired, substitute the passenger's name for each passenger number instead of referring to the different passengers merely as "passenger 1", "passenger 2", etc. In steps 706-721 the user is incrementally prompted for personal flight data for each passenger such as the flight parameters corresponding to $SAO_2$ levels below about 91% as previously discussed. It is noted that the flight parameters necessary to obtain useful personal flight data may vary, since the logic device can convert a multitude of flight parameter values to a common parameter, such as $PO_2$, by use of the formulas previously provided. This personal flight data, if available, may be manually input into device 400 with the input device 402, provided to the logic device of device 400 by the storage medium that is connected to interface 412 of device 400 and decoded by a reading device which is inside of device 400, the reading device providing the decoded information to the logic device, or provided to the logic device by virtue of data communications between the adapter 408 or the antenna 410 of device 400. Thus, upon the user being prompted for personal flight data for a passenger 1 in step 706, if the personal flight data is available from any of the previously identified sources, it is provided to the logic device 400 in step 709, otherwise the user is queried in step 712 to provide estimated personal flight data for passenger 1 or have the device provide this information. If the user provides personal flight data for passenger 1, this information is input into device 400 in step 718, otherwise in step 715, the microprocessor of device 400 provides the estimated personal flight data for passenger 1. The information to estimate flight data is preloaded into the logic device, and may optionally be based on the degree of conservatism of the user. That is, if the user wishes to be provided with oxygen requirement information which is on the conservative side, the logic device will provide more conservative personal flight data for passenger 1. Optionally, however, the logic device may query the user for information about passenger 1, such as age, height, and weight and gender, and provide estimated personal flight data for passenger 1 based at least partly upon this information. Also, if the user has not flown for an extended prior of time, but has some previous flight information, and some user information, such as age, gender, weight, for both the previous flight as well as current user information, the logic device may be able to provide estimated personal flight data based at least partly upon this information. Once the personal flight data has been provided for all passengers, satisfying step 721, the user is directed to input particulars of each leg of the flight, starting in step 724. Optionally, the user may be prompted to provide a range of personal flight data values for each passenger, whether established or estimated, which may be expressed in percent, such as a percent of $PO_2$, or a number of feet of cabin pressure density altitude, for example, from which the logic device would calculate a range of values from the provided personal flight data corresponding to $SAO_2$ values of less than about 91%. This range could also be used to provide a more conservative oxygen requirement estimate, if desired. In case there is sufficient personal flight data to establish such a range, this range could be used unless the user directs otherwise.

Figure 12:
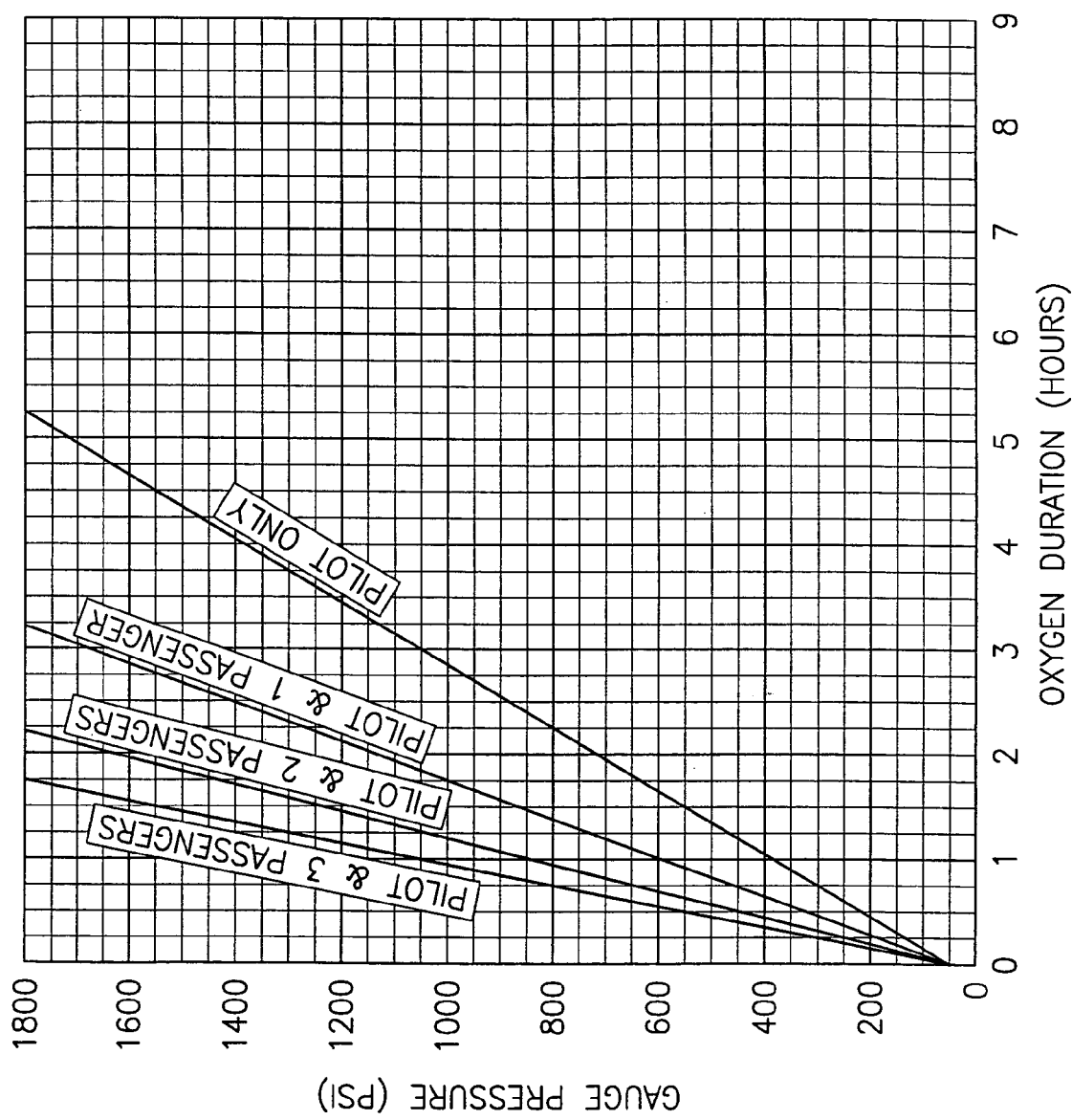
FIG. 12 is a graph illustrating oxygen usage durations plotting on-board gage pressure of oxygen versus time.

Continuing to refer to the oxygen planning portion in FIGS. 13A-13B, in step 724 the user is prompted to provide the number of legs of the proposed flight. The user is then prompted in step 727 for particulars of a flight leg, providing such information as altitude, distance and speed, or altitude and then identifying two geographic reference points so that distance may be determined, and speed. Once the user has provided the particulars for each leg of the flight, satisfying step 730, in step 731 the user is then prompted to provide the type, model, and date of manufacture of the aircraft. Typically, a particular type, model, and year of manufacture corresponds to a specific type of on-board oxygen tank and dispensing system. This information is preloaded into the logic device. In step 733, the logic device, having stored therein information similar to the data contained in FIG. 12 which correlates the pressure in the on-board oxygen tank in the aircraft to oxygen duration, depending upon the number of passengers in the aircraft, then calculates oxygen requirements for each passenger for each leg of the flight, the cumulative oxygen requirements, and the remaining oxygen upon completion of the flight and outputs this information to the output device 404 in step 736.

Figure 13C:
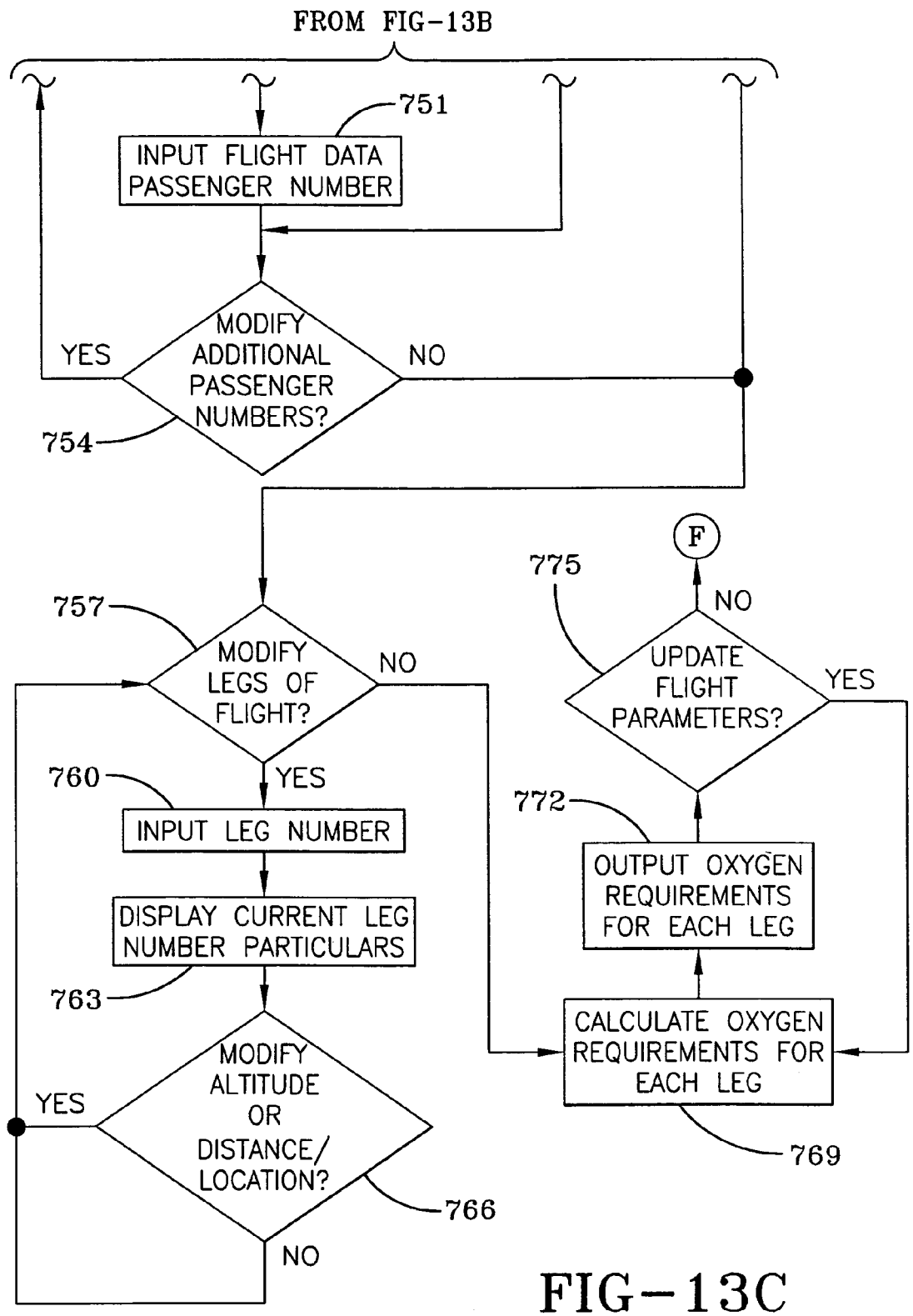
FIG. 13C is a diagram of a modification branch of the oxygen planning procedure of the present invention.

Once the oxygen requirements have been provided, the user is directed to the modification portion in FIGS. 13B-13C and is afforded the opportunity to selectively modify personal flight data for any passenger, modify any of the particulars of any of the flight legs, or modify any flight parameters. Such modification options permit the user to observe the effects these modifications have on oxygen requirements. For example, a proposed flight plan may require more oxygen than the aircraft can carry. Once alerted to this fact, the user may alter any of the flight leg altitudes, or even remove a passenger from the flight.

The modification portion in FIG. 13C which begins at step 739 queries the user if personal passenger data modifications are desired. If modifications are desired, in step 740 the user is queried if passengers are being added or removed from the flight. If passengers are to be either added or removed, in step 741 the user is prompted to select the desired modifier, that is, "add" or "remove", and then identify the passenger if the passenger is being removed. In step 742 the user is directed to either confirm or not confirm the proposed information for addition or removal from step 741, and irrespective of the user's choice regarding confirmation of the addition or removal information in step 742, the user is directed to step 740 for further passenger additions or removals, if desired. Once the user wishes to make no further passenger additions or removals, the user is directed in step 743 to determine whether the user wishes to modify the personal flight data for any of the passengers. If the user does not wish to modify the personal flight data for any of the passengers, the user is directed to step 757, otherwise, the user is directed in step 744 to identify the particular passenger whose personal flight data requires modification. The user is then queried in step 745 whether the user wishes to provide the modified personal flight data, or whether the user wishes the device 400 to provide this information. If the user wishes to provide the personal flight data, in step 751 the user is permitted to input this information with the input device 402. However, if the user elects for the device 400 to provide this information, in step 748 the device 400 is permitted to do so, preferably after prompting the user for clarifying information containing physical information about the particular passenger as previously discussed. Once the personal flight data information has been modified, whether by the user or by the device 400, in step 754 the user is then offered the opportunity to modify the personal flight data information for other passengers. If the user elects to further modify this information for other passengers, the user is returned to step 743 to repeat the procedure as previously discussed, otherwise the user is directed to the portion of the modification procedure relating to flight legs, beginning at step 757.

In the modification procedure relating to flight legs, in step 757 the user is offered the opportunity to modify an aspect of a flight leg. If the user does not wish to modify any of the flight leg information, the user is directed to step 769. However, if the user elects to modify flight leg information, in step 760 the user is queried to select a particular leg of the flight. Upon the user selecting a particular flight leg, in step 763 the specific information for the particular leg is output to the output device 404, and then in step 766 the user is queried to modify any of the specific information for the particular leg. Whether or not the user makes any modifications to the flight leg information, the user is directed to step 757 with the option of making further flight leg modifications. Once the user wishes to make no more changes to the flight legs, the user is directed to step 769 where the oxygen requirements for each leg are calculated, and in step 772 the oxygen requirements both for each leg and cumulative oxygen requirements as previously discussed are output to output device 404. In step 775 the user is then queried whether further updates to any flight parameters are desired. If the user requires further updates, the user is directed to step 452 of the first mode of operation in FIG. 9 wherein the user is again offered the opportunity to modify flight parameters as previously discussed, followed by similar opportunities to further modify the number of passengers, the passengers' personal flight data, or flight leg information as previously discussed.

Figure 10:
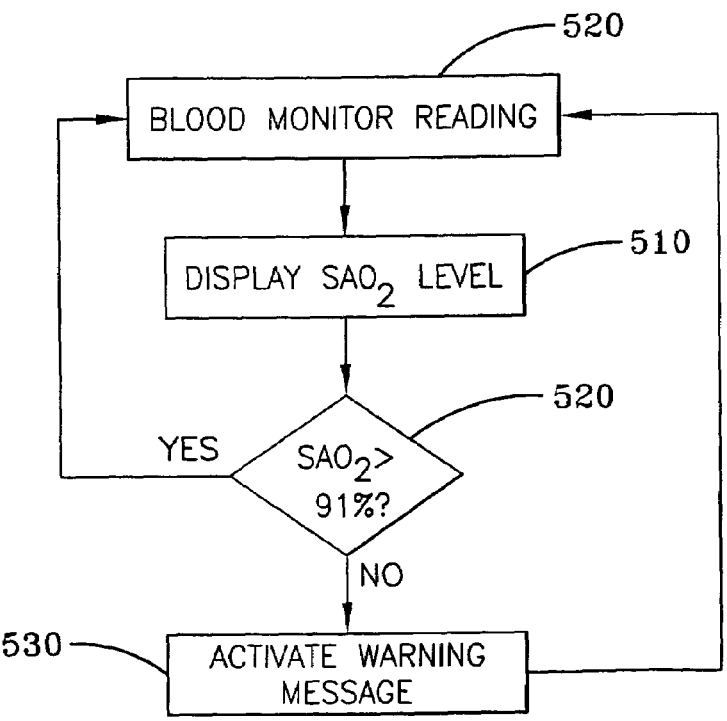
FIG. 10 is a diagram of an independent loop of the first operating mode of the device of the present invention.

Operating independently of the first operating mode in FIG. 9 is FIG. 10 which relates to providing periodic blood oxygen monitor readings if device 400 is equipped with a blood oxygen monitor. If device 400 is so equipped, the clip 406 extending from device 400 is secured to the thumb or other compatible appendage of the user for taking periodic blood saturation readings, namely $SAO_2$, in step 500. Once the $SAO_2$ reading has been taken, in step 510 the value of the reading is output to output device 404 of the device 400. In step 520 the $SAO_2$ value is compared to the 91% threshold standard. If the standard is met, the monitor takes another $SAO_2$ reading at a predetermined period of time after the previous reading. However, if the value of the reading is less than 91%, in step 530 the warning device in device 400 is activated, such as an audio speaker or vibrating instrument, to alert the user of this condition. As previously discussed in the system, the warning device may reset, or if the value remains below 91% may be combined with other warnings.

Figure 11A:
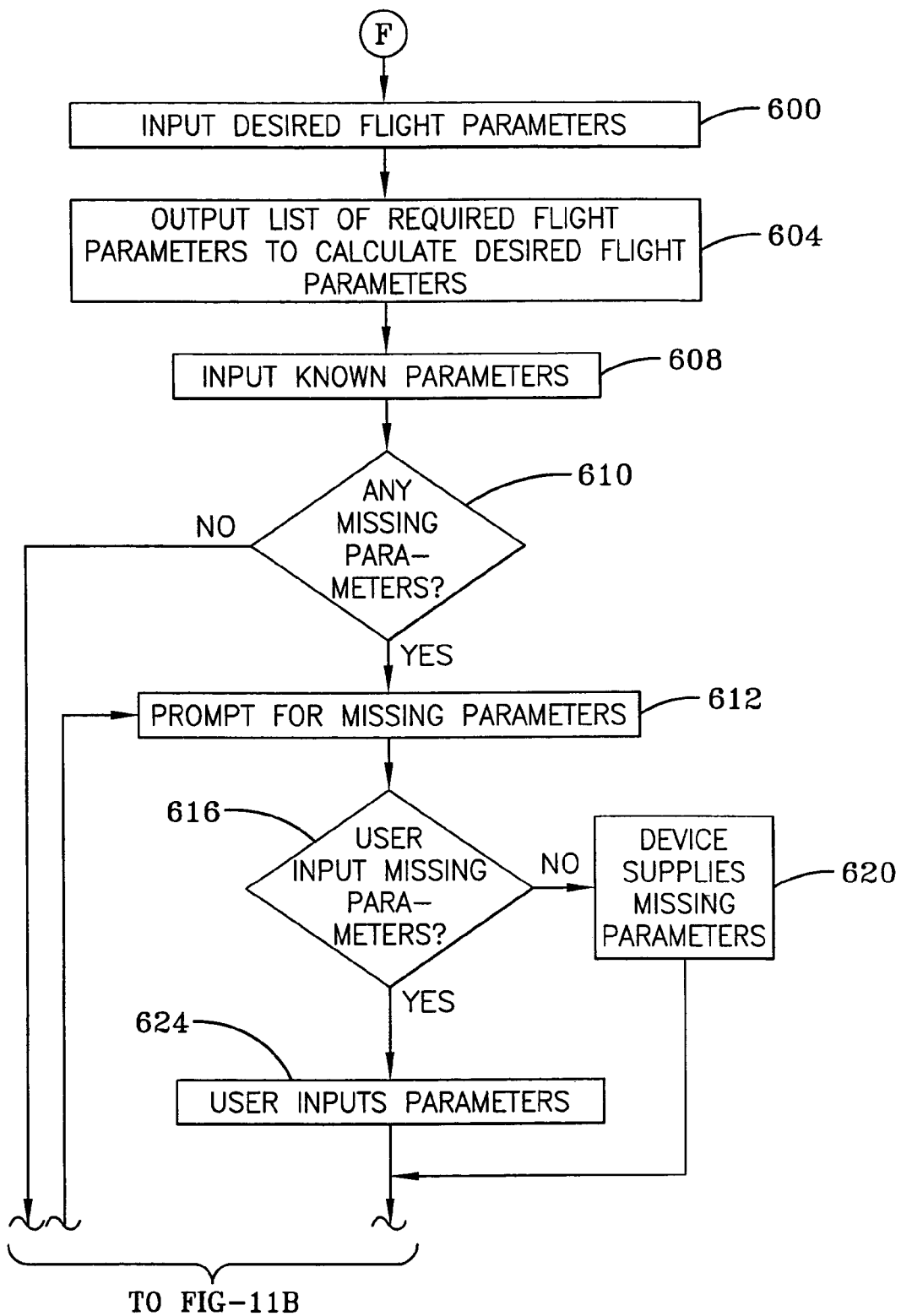
FIGS. 11A-11B is a diagram of a second operating mode of the device of the present invention.
Figure 11B:
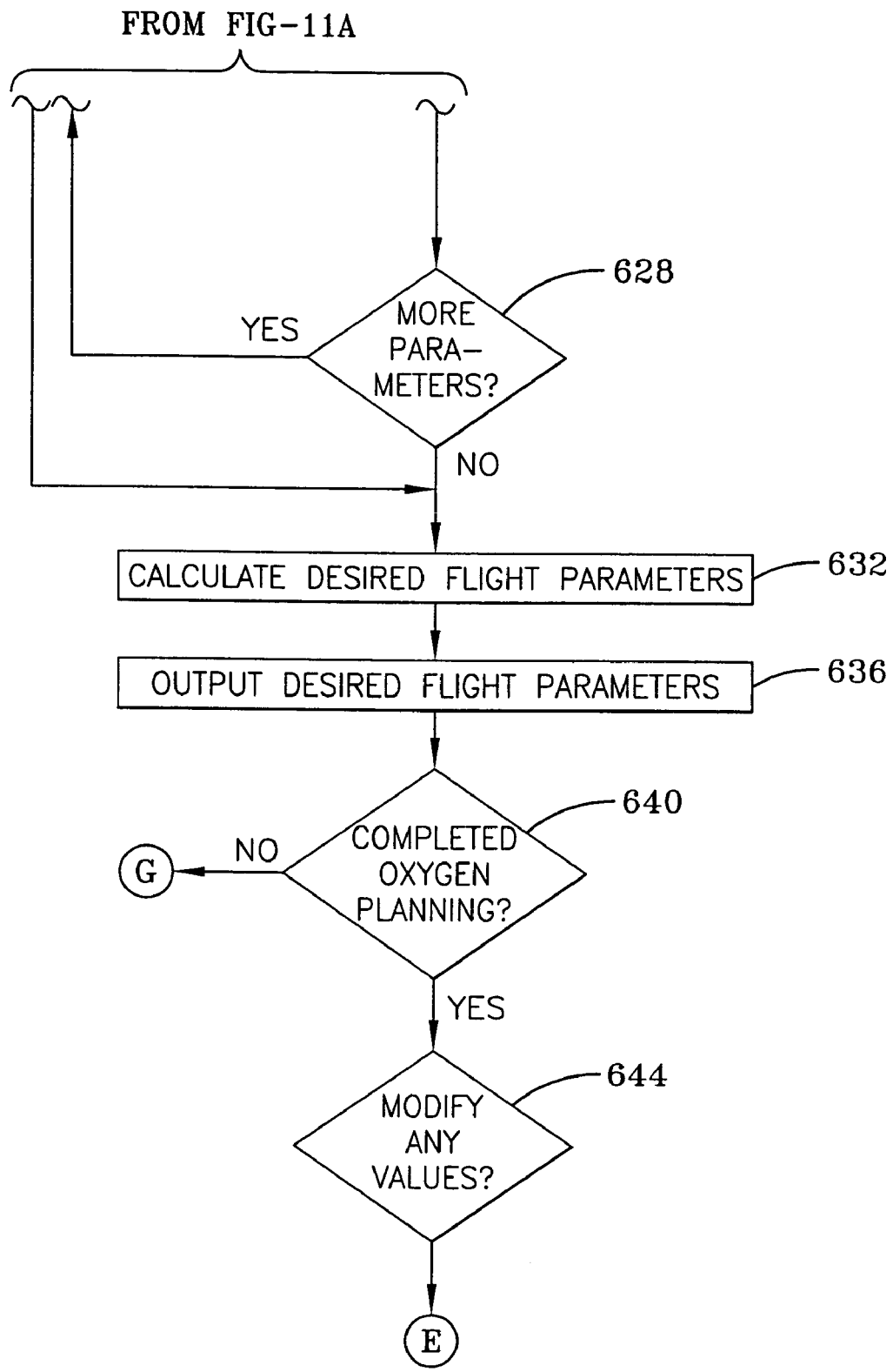

The second operating mode of device 400, referring to FIGS. 11A-11B, prompts the user to input desired parameters in step 600 that the user would like for device 400 to calculate. Once the user has input the desired parameters, in step 604 the logic device identifies the parameters that must be provided to permit the logic device to calculate the desired parameters. The list of desired parameters in step 604 is then output to the output device 404. The user is prompted in step 608 to input known values for as many of the listed parameters as possible. Once the user has supplied values in step 608 for all listed parameters that are known to the user, the device 400 determines whether there are any remaining parameters which the user has not provided a value. If there are no remaining parameters, the user is directed to step 632, otherwise, the user is then prompted in step 612 to supply values for each of the remaining or "missing" parameters. For each missing parameter, in step 616 the user is prompted to either provide a value or have the device 400 provide a value for the missing parameter. If the user elects to provide the value of the missing parameter, in step 624 the user inputs the value for the missing parameter. However, if the user elects for the device 400 to provide the value of the missing parameter, in step 620 the logic device of device 400 selects a value, preferably by querying the user for additional information in order to provide a more accurate estimated value for the missing parameter. After the logic device has provided a value for the missing parameter, in step 628 the user is directed to step 612 to provide a value for another missing parameter if any remain. However, once values have been selected for all the missing parameters, the logic device in device 400 in step 632 calculates the desired flight parameters, and outputs the list of the desired flight parameters to the output device 404 in step 636. Once step 636 is completed, in step 640 the user is directed to the oxygen planning procedure in FIGS. 13A-13B as previously discussed if the user has not previously been directed there, otherwise in step 644, the user is directed to the modification branch in FIG. 13C also as previously discussed. The independent procedure in FIG. 10 relating to blood oxygen monitoring as previously discussed remains applicable if the device 400 is equipped with the monitoring clip 406.

Preferably, the device 400 can easily toggle between the first and second operating modes. A determining factor for selecting one operating mode over the other is whether the user knows which flight parameters for the device 400 to calculate and whether the user knows the values for the information required to calculate those flight parameters. For example, in the first operating mode, the user inputs all the known parameter values into the device 400. Only flight parameter values that are calculable by the logic device based solely upon the known parameter values are provided for selection by the user. However, if the user discovers that the parameter he seeks does not appear while using the first operating mode, upon switching to the second operating mode, the user may then identify that flight parameter of interest, and a list of parameters required to obtain a value for the parameter of interest will then be provided by device 400 to the user. Additionally, in the second operating mode, missing flight parameters are identified and the user is given the option to either provide a value for each of the missing parameters or have the device provide a value for the missing parameter, preferably prompting the user for additional information to provide a more accurate estimated value. In either operating mode, the user may modify at any time any flight parameter value, including the number of passengers.

The oxygen requirement estimating device of the present invention advantageously provides a high degree of flexibility for incorporating flight parameter modifications, even permitting the user to modify flight parameters affecting oxygen flight requirement while the flight is ongoing. Thus, changing weather conditions may be taken into account, including altered flight leg parameters, such as distance and altitude, and the incremental as well cumulative oxygen requirements may be readily calculated. In addition to the flexibility provided, the oxygen planning device is based on the monitoring system which provides unprecedented levels of protection to the passengers against the possibility of hypoxemia.

Although one having ordinary skill in the art will realize that the system of the present invention is primarily directed to humans, certain mammals, such as primates, and quite possibly many other animals may likewise be able to utilize similar clinical standards to their benefit in case they must be subjected to unpressurized flight.

The present invention also contemplates usage with pressurized cabins since even pressurized cabins correlate to cabin pressure altitudes ranging from about 4,000 to about 8,000 feet. Such usage may be recommended for longer flights, such as transcontinental or international flights, preferably contiguous flights wherein the passengers are exposed to the cabin pressure altitudes for extended periods of time without relief. More specifically, the safety system may be employed to address a condition known as "passenger rage" in which a passenger, possibly due to adverse effects of hypoxia, may lose his compose and require restraint. By monitoring passengers of longer duration flights, those susceptible to a slightly reduced atmospheric pressure level, combined with dehydration, which may be further exacerbated by alcohol consumption, this condition may be avoided, further enhancing aircraft safety.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A system for use in an aircraft for avoiding hypoxemia in at least one subject exposed to a reduced atmospheric pressure, the system comprising:

an air source to supply an oxygen mixture to at least one subject;

a microprocessor being configured to determine an increased risk of hypoxemia in the at least one subject and atmospheric conditions corresponding to hypoxemia in the at least one subject, the microprocessor activating the air source to provide the oxygen mixture to the at least one subject in response to a determination of the increased risk of hypoxemia or atmospheric conditions corresponding to the increased risk of hypoxemia in the at least one subject;

a first sensor to measure at least one physiological characteristic of the at least one subject, the first sensor transmitting a first signal to the microprocessor with the at least one physiological characteristic of the at least one subject;

wherein the microprocessor determines the increased risk of hypoxemia in the at least one subject by comparing the at least one physiological characteristic of the at least one subject with a predetermined value for the at least one physiological characteristic of the at least one subject, the microprocessor determining the increased risk of hypoxemia in response to the at least one physiological characteristic of the at least one subject being less than the predetermined value for the at least one physiological characteristic; and a first time reference measured from an instant the oxygen mixture is first being provided to the at least one subject, the at least one subject being required to perform an affirmative act to reset the first time reference, the first time reference being compared to a second predetermined period of time, wherein in response to the first time reference exceeding the second predetermined period of time, emergency procedures are initiated, the emergency procedures include transmitting an automatic emergency message to a pre-programmed airport tower.

2. The system of claim 1 wherein the at least one physiological characteristic is an oxygen red cell saturation level for arterial circulation.

3. The system of claim 2 wherein the predetermined value for the oxygen red cell saturation level is about 91 percent.

4. The system of claim 1 wherein the system is portable.

5. The system of claim 4 wherein the system is substantially incorporated within a single container.

6. The system of claim 1 wherein the system is for use in an aircraft having an unpressurized cabin.

7. The system of claim 1 further comprising a second sensor to measure at least one atmospheric pressure of an area surrounding the at least one subject, the second sensor transmitting a second signal to the microprocessor with the at least one atmospheric pressure of an area surrounding the at least one subject, wherein the at least one physiological characteristic measurement and the at least one atmospheric pressure measurement are measured at substantially the same instant in time.

8. The system of claim 7 wherein the at least one atmospheric pressure is measured pressure altitude in lineal units mean sea level.

9. The system of claim 7 further comprising a storage device having at least one previously stored physiological characteristic measurement and an atmospheric pressure measurement measured at substantially the same instant of time as the at least one stored physiological characteristic measurement of the at least one subject, the storage device transmitting a third signal to the microprocessor, the microprocessor determining atmospheric conditions corresponding to the increased risk of hypoxemia by comparing the atmospheric pressure measurement of the at least one previously stored physiological characteristic measurement with the at least one atmospheric pressure of the area surrounding the at least one subject, and the microproccesor determining atmospheric conditions corresponding to hypoxemia in response to the atmospheric pressure measurement of the at least one previously stored physiological characteristic measurement exceeding the at least one atmospheric pressure of the area surrounding the at least one subject.

10. The system of claim 9 wherein the storage device is remote from the at least one subject.

11. The system of claim 1 wherein the microprocessor is remote from the at least one subject.

12. The system of claim 1 further comprising a warning device for providing at least one warning message to the at least one subject in response to receiving a signal from the microprocessor.

13. The system of claim 12 wherein the at least one warning message is a signal in the form of an audio signal, a visual signal, a signal convertible to provide a tactile sensation or any combination thereof for the at least one subject.

14. The system of claim 1 wherein the atmospheric conditions are obtained from personal flight data from the at least one subject.

15. A system for use in an aircraft for avoiding hypoxemia in at least one subject exposed to a reduced atmospheric pressure, the system comprising:

an air source to supply an oxygen mixture to at least one subject;

a microprocessor being configured to determine an increased risk of hypoxemia in the at least one subject and atmospheric conditions corresponding to hypoxemia in the at least one subject, the microprocessor activating the air source to provide the oxygen mixture to the at least one subject in response to a determination of the increased risk of hypoxemia or atmospheric conditions corresponding to the increased risk of hypoxemia in the at least one subject;

a first sensor to measure at least one physiological characteristic of the at least one subject, the first sensor transmitting a first signal to the microprocessor with the at least one physiological characteristic of the at least one subject;

wherein the microprocessor determines the increased risk of hypoxemia in the at least one subject by comparing the at least one physiological characteristic of the at least one subject with a predetermined value for the at least one physiological characteristic of the at least one subject, the microprocessor determining the increased risk of hypoxemia in response to the at least one physiological characteristic of the at least one subject being less than the predetermined value for the at least one physiological characteristic; and a first time reference measured from an instant the oxygen mixture is first being provided to the at least one subject, the at least one subject being required to perform an affirmative act to reset the first time reference, the first time reference being compared to a second predetermined period of time, wherein in response to the first time reference exceeding the second predetermined period of time, emergency procedures are initiated, the emergency procedures include automatically decreasing the aircraft altitude.

16. A system for use in an aircraft for avoiding hypoxemia in at least one subject exposed to a reduced atmospheric pressure, the system comprising:

an air source to supply an oxygen mixture to at least one subject;

a microprocessor being configured to determine an increased risk of hypoxemia in the at least one subject and atmospheric conditions corresponding to the increased risk of hypoxemia in the at least one subject and to control the air source to provide the oxygen mixture to the at least one subject in response to the determination of the increased risk of hypoxemia or atmospheric conditions corresponding to the increased risk of hypoxemia in the at least one subject;

a pulse oximeter to measure at least one oxygen red cell saturation level for arterial circulation of the at least one subject, the pulse oximeter transmitting a first signal to the microprocessor with the at least one oxygen red cell saturation level for arterial circulation of the at least one subject;

wherein the microprocessor determines the increased risk of hypoxemia in the at least one subject by comparing the at least one oxygen red cell saturation level for arterial circulation of the at least one subject with a predetermined value of about 91 percent for the at least one oxygen red cell saturation level for arterial circulation of the at least one subject, the microprocessor determining the increased risk of hypoxemia in response to the at least one oxygen red cell saturation level for arterial circulation of the at least one subject being greater than the predetermined value for the at least one oxygen red cell saturation level for arterial circulation; and a first time reference measured from an instant the oxygen mixture is first being provided to the at least one subject, the at least one subject being required to perform an affirmative act to reset the first time reference, the first time reference being compared to a second predetermined period of time, wherein in response to the first time reference exceeding the second predetermined period of time, emergency procedures are initiated, the emergency procedures include transmitting an automatic emergency message to a pre-programmed airport tower.

* * * * *

UNITED STATES PATENT AND TRADEMARK OFFICE
CERTIFICATE OF CORRECTION

PATENT NO. : 7,246,620 B2  Page 1 of 1
APPLICATION NO. : 10/697785
DATED : July 24, 2007
INVENTOR(S) : John D. Conroy, Jr.

It is certified that error appears in the above-identified patent and that said Letters Patent is hereby corrected as shown below:

In column 8, line 38, "substemal" should be -- substernal --

Signed and Sealed this

Twentieth Day of November, 2007

JON W. DUDAS
*Director of the United States Patent and Trademark Office*